(12) United States Patent
Hettiarachchy

(10) Patent No.: US 8,575,310 B2
(45) Date of Patent: Nov. 5, 2013

(54) BIOACTIVE PENTAPEPTIDES FROM RICE BRAN AND USE THEREOF

(75) Inventor: Navam S. Hettiarachchy, Fayettville, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 135 days.

(21) Appl. No.: 12/954,285

(22) Filed: Nov. 24, 2010

(65) Prior Publication Data

US 2011/0152180 A1 Jun. 23, 2011

Related U.S. Application Data

(60) Provisional application No. 61/287,517, filed on Dec. 17, 2009.

(51) Int. Cl.
| | |
|---|---|
| C07K 4/00 | (2006.01) |
| C07K 4/10 | (2006.01) |
| C07K 1/113 | (2006.01) |
| C12N 15/00 | (2006.01) |

(52) U.S. Cl.
USPC .......................... 530/330; 530/345; 435/69.1

(58) Field of Classification Search
None
See application file for complete search history.

(56) References Cited

PUBLICATIONS

Genistein, http://www.genistein.net/index.html, accessed Jul. 16, 2012.*
Gura (Science, v278, 1997, pp. 1041-1042).*
Freshney (Culture of Animal Cells, A Manual of Basic Technique, Alan R. Liss, Inc., 1983, New York, p. 4).*
Dermer (Bio/Technology, 1994, 12:320).*
Margoni et al. (2012, Int. J. Biochem. Cell Biol. 44:475-479).*
Lukiw (2012, Expert Opin. Emerging Drugs 17:43-60).*
Hettiarachchy, N.S., Griffin, V.K., and Gnanasambandam, R. 1996. Preparation and Functional Properties of a Protein Isolate from Defatted Wheat Germ. Cereal Chem. 73(3):363-367.
Anderson, A., Hettiararchchy, N.S., and Ju, Z. Y. 2001. Physicochemical properties of pronase-treated rice glutelin. J. Am. Oil Chem. Soc. 78:1. 1-6.
Ilankovan P., Hettiarachchy, N.S., and Christian S. 2007. Preparation of Rice Endosperm Protein Isolate by Alkali Extraction. Cereal Chemistry, Manuscript ID CC-05-07-0094, accepted for publication on Aug. 20, 2007.
Ilankovan P., Hettiarachchy, N.S., and Christian S., and Markus I. B. 2007. Hydrophobicity, solubility and emulsifying properties of enzyme modified rice endosperm protein, Cereal Chemistry, 84(4):343-349.
Ilankovan P., Hettiarachchy, N.S., and Christian S. 2007. Glycosylation and deamidation of rice endosperm protein for improved emulsifying properties, Cereal Chemistry, Manuscript ID CC-04-07-0068, accepted for publication on Jun. 29, 2007.
Tang, S. 2002. Optimization of protein extraction system and protein functionalities for heat-stabilized defatted rice bran. Ph.D Thesis, p. University of Arkansas, Fayetteville, Arkansas.
Tang, S., Hettiarachchy, N.S., and Shellhammer, T.H. 2002. Protein extraction from heat-stablized defatted rice bran. 1. Physical processing and enzyme treatments. J. Agric. Food Chem. 50:7444-7448.

(Continued)

*Primary Examiner* — Elizabeth C Kemmerer
(74) *Attorney, Agent, or Firm* — Head, Johnson & Kachigian, P.C.

(57) ABSTRACT

In general, the invention relates to novel bioactive pentapeptides from heat stabilized defatted rice bran having anti-cancer, anti-obesity, anti-Alzheimer and other health-promoting activities proteins. The bioactive pentapeptides can be incorporated into pharmaceutical, nutraceuticals and food compositions having at least the bioactive pentapeptide as an active ingredient.

8 Claims, 12 Drawing Sheets

(56) References Cited

PUBLICATIONS

Tang, S., Hettiarachchy, N.S., Eswaranandam, S., and Crandall, P. 2003a. Protein extraction from heat stablized defatted rice bran. 11. The role of amylase, celluclast, and viscoyme. J. Food Sci. 68(2):471-475.

Wang, M., Hettiararchchy N.S., Qi M., Burks W., Siebenmorgen T.,1999. Preparation and functional properties of rice bran protein isolate. J. Agri Food Chem. 47:4111-416.

Arvind Kannan, Navam Hettiarachchy, Satya Narayan. Colon and Breast Anti-cancer Effects of Peptide Hydrolysates Derived from Rice Bran. 2009. The Open Bioactive Compounds Journal, , 2, 17-20.

Arvind Kannan, Navam Hettiarachchy, Michael G. Johnson, Ramakrishna Nannapaneni. 2008. Human Colon and Liver Cancer Cell Proliferation Inhibition by Peptide Hydrolysates Derived from Heat-Stabilized Defatted Rice Bran. J Agric Food Chem 56 (24), 11643-11647.

* cited by examiner

Values are means of two trials ± SE. Values not connected by same letters are significantly different ($P<0.05$)
-ve control: saline
+ve control: Genistein (200μM, 400μM)

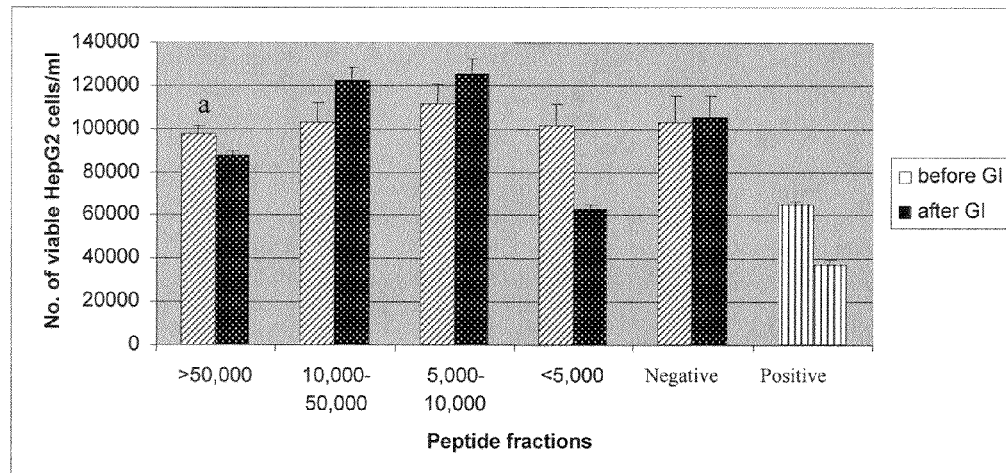

Figure 3
Values are means of two trials ± SE. Values not connected by same letters are significantly different (P<0.05)
-ve control: saline with 0.1% methanol
+ve control: Genistein (200µM, 400µM) in saline with 0.1% methanol

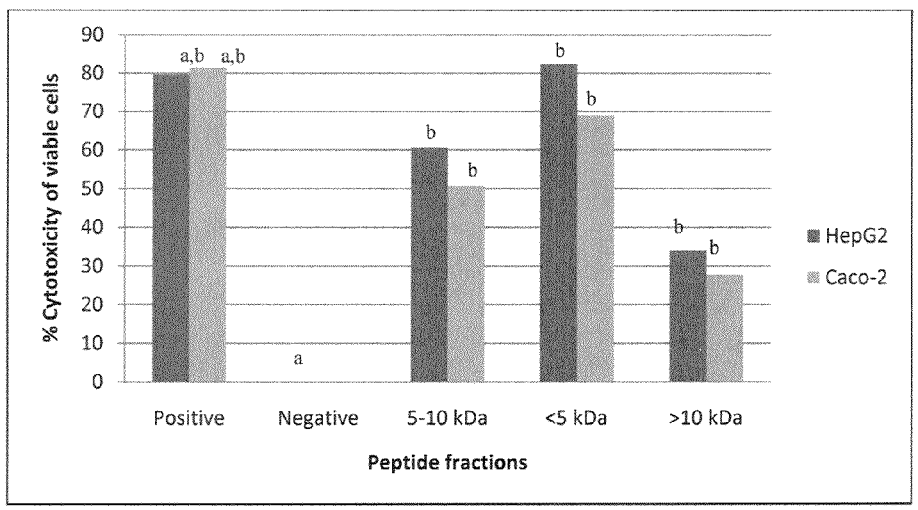

Figure 4
Values are means of two trials ± SE. Values not connected by same letters are significantly different (P<0.05).
MTS - (3-(4,5-dimethylthiazole-2-yl)-5-(3-carboxymethoxyphenyl)-2-(4-sulfophenyl)-2H-tetrazolium
Negative: saline
Positive: Genistein (200µM).

100mM: 100mM NaCl eluate; 50 mM: 50mM NaCl eluate
Values are means trials ± SE. Values not connected by same letters are significantly different (P<0.05),
Negative (viability control): saline; Positive (inhibitory control): Genistein (400µg/ml) .
MTS - (3-(4,5-dimethylthiazole-2-yl)-5-(3-carboxymethoxyphenyl)-2-(4-sulfophenyl)-2H-tetrazolium Values are means trials ± SE. Values not connected by same letters are significantly different (P<0.05), MTS - (3-(4,5-dimethylthiazole-2-yl)-5-(3-carboxymethoxyphenyl)-2-(4-sulfophenyl)-2H-tetrazolium
Negative (viability control): saline
Positive (inhibitory control): Genistein (400μg/ml)
Peptide fractions 1mg/ml Values are means trials ± SE. Values not connected by same letters are significantly different (P<0.05), MTS - (3-(4,5-dimethylthiazole-2-yl)-5-(3-carboxymethoxyphenyl)-2-(4-sulfophenyl)-2H-tetrazolium
Negative (viability control): saline
Positive (inhibitory control): Genistein (400μg/ml)

x-axis: mass to charge ratio (m/z); y-axis: intensity
Molecular mass of the peptide identified to be 685.378 daltons.
Inset: Purified peak at 62min elution from HPLC.

BIOACTIVE PENTAPEPTIDES FROM RICE BRAN AND USE THEREOF

CROSS-REFERENCE TO RELATED APPLICATIONS

This application claims priority to U.S. Provisional Application Ser. No. 61/287,517, "Protein Hydrolysates and Peptides with Anticancer Activities from Rice Bran and Methods of Preparation Thereof," filed Dec. 17, 2009, which is incorporated in its entirety herein by reference.

BACKGROUND OF THE INVENTION

1. Field of the Invention

This invention relates generally to bioactive proteins, peptides and enzymatic hydrolysates from rice bran and use thereof, and more particularly to a purified, unmodified and modified bioactive pentapeptide from heat stabilized defatted rice bran having anti-cancer, anti-obesity, anti-Alzheimer and other health-promoting activities. The bioactive pentapeptides can be incorporated as an active ingredient into pharmaceutical, nutraceutical and food compositions.

2. Description of the Related Art

The treatment of cancer, obesity-related and age-related chronic diseases are life-long and can have side effects. Americans are supplementing traditional health care by turning to nutraceuticals and functional foods. Nutraceuticals are considered safe, effective and ingestible for a lifetime without toxicity, reversibly inhibiting type and, also amenable to clinical trials. These, when proven effective, can function as alternatives to high-cost prescriptions, and could be the next generation natural anti-disease agents delivered at low cost and high efficacy. The use of nutraceuticals in foods, beverages and supplements is well established in Japan and is gaining interest in the United States.

In the United States, cancer is the second most leading cause of death. The Centers for Disease Control and Prevention (CDC) estimated nearly 1.4 million new cases of cancer in 2008 and half a million deaths due to cancer occurred in 2007. Colorectal cancer is the second leading cause of cancer-related death in the United States. Over the past decade, the incidence of colorectal cancer has not decreased, and hence there has been no improvement in the mortality rate. Treatment and preventive options for colorectal cancer mainly focus on early detection. There is evidence that dietary components are one of the most important environmental factors in the cause of the colorectal cancer and hence may act as suitable markers or dietary determinants, which when modified and prepared in a biofunctional form can serve as bioactive compounds in reducing the incidence of colorectal cancers. Liver cancer is the most common cancer type in developing countries, but is less common (2% of cancer deaths) in United States, affecting twice as many men as women. The American Cancer Society has estimated 21,370 new cases in 2008 with 18,410 liver-cancer-related deaths in the United States in 2007. Chemotherapy, radiotherapy and liver transplantation are the treatment options available for treating liver cancer. As alternative treatment, to reduce the risk of developing cancer, the focus is on identifying compounds present in natural foods that could bear anti-liver cancer properties.

In addition to cancer, the risk of chronic complications from obesity-related diseases is a leading cause of death in the United States. The growing epidemics of type-2 diabetes and cardiovascular disease are linked to obesity, and in fact, nearly 90% of diabetics are caused by obesity. Consequently, obesity has triggered impaired glucose tolerance in nearly 197 million people worldwide. Estimated cases of diabetes in the United States currently stand at 19.2 million comprising 30-40% of world's type-2 diabetics. Roughly 63.1% of Americans have been identified to be obese with a basal metabolic index (BMI) of at least 25.0. In particular, childhood obesity in the United States has tripled in the past two (2) decades.

Following the ranks of cancer and cardiovascular disease and their related complications in causing death, is a neurological disorder, Alzheimer's disease. It has been thought that blood vessel damage in the brain, most likely to occur in patients with diabetes and high cholesterol, can lead to symptoms of Alzheimer's disease and, preventing these states can reduce the risk of developing Alzheimer's disease. One (1) in eight (8) persons aged 65-85 and nearly half of persons over age 85 have Alzheimer's disease. In 2011, baby boomers (those born between 1946 and 1964) will begin turning 65, reaching the age that stratifies greatest risk for Alzheimer's disease. To reduce the risk for Alzheimer's disease, many have turned to alternative treatments based on compounds present in natural foods that could bear anti-Alzheimer's disease properties.

Several bioactive components in nutraceuticals have demonstrated anti-oxidant, anti-obesity, anti-angiogenic and anti-hypertensive activities and hypocholesterolemic and immunomodulatory effects. Peptides and proteins from food sources can aid in cancer prevention and treatment. For example, whey proteins and α-lactalbumin have been shown to inhibit colon cell proliferation. Cereal grains and their components are widely investigated for the presence of bioactive components to be used in nutraceuticals. Cereal grains are known to possess high-quality protein, which when consumed, are broken down by gastrointestinal (GI) proteolytic enzymes to release bioactive peptides. Cereal grains including rice, wheat and legumes, including soybeans, and their respective components, have been investigated for the presence of bioactive proteins and peptides. For example, Oryzatensin, an ileum-contracting bioactive peptide obtained from rice albumin, has been shown to have an immuno-stimulatory role. Similarly, proteolytic hydrolysis of soybean protein using Alcalase and Proteinase S enzymes resulted in peptides that were anti-hypertensive and anti-oxidative, respectively. Rice and its components have also been studied to exert specific anti-disease properties, such as anti-oxidative, anti-carcinogenic and anti-mutagenic. Constituents such as proteins and peptides from rice or co-products of rice milling, however, have only been studied to a limited extent.

Enzymatic hydrolysis has been one of the main approaches to produce bioactive peptides from soybean, wheat, corn, rice, barley, buckwheat and sunflower proteins. The potential bioactive nature of components of rice, however, is not well known, including the bran portion, which is nutritionally beneficial but used as a low cost animal feed. It is also important that the peptides be resistant to GI environment when ingested for being metabolically bioactive.

Rice bran is a cheap co-product of rough rice milling having nutrients including B vitamins, minerals, and fiber, including oil, which has health benefits. It is being used as a low-cost animal feed and the state of Arkansas contributes over 50% of the overall rice production in the United States. Defatted rice bran has approximately 20% protein, with the proteins and their peptide fragments being complexed within carbohydrates and lipids providing difficulties in protein extraction.

It is therefore desirable to provide bioactive proteins, peptides and enzymatic hydrolysates from rice bran and use thereof.

It is further desirable to provide a purified, unmodified and modified bioactive pentapeptide from heat stabilized defatted rice bran having anti-cancer, anti-obesity, anti-Alzheimer and other health-promoting activities.

It is yet further desirable to provide bioactive pentapeptides that can be incorporated as an active ingredient into pharmaceutical, nutraceutical and food compositions.

It is still further desirable to provide bioactive pentapeptides having unique sequences that renders its bioactive nature, which can enhance glucose uptake into cells, act to sequester bad cholesterol and fatty acids accumulating in excessive BMI states, or even mitigate molecular events taking place in neuronal cells during the onset of Alzheimer's disease.

SUMMARY OF THE INVENTION

In general, in a first aspect, the invention relates to a bioactive pentapeptide comprising the amino acid sequence Glu-Gln-Arg-Pro-Arg (SEQ ID NO: 1). The bioactive pentapeptide may be isolated from heat stabilized defatted rice bran or non-defatted rice bran, and exhibits anti-cancer, anti-obesity and/or anti-Alzheimer activity. The anti-cancer activity of the bioactive pentapeptide may be an inhibitory activity on proliferation of human colon, liver, breast and/or lung cancer cell lines. The bioactive pentapeptide may be modified, including: the side chain glutamine group being glycosylated, methylated or modified by deamidation; the side chain glutamic acid group and the side chain glutamine group being modified to form a pyroglutamate acid-peptide; and at least one side chain arginine group being modified with a food grade dicarbonyl substance.

In general, in a second aspect, the invention relates to a pharmaceutical composition comprising the bioactive pentapeptide and a pharmaceutically acceptable carrier. The pharmaceutical composition may be for topical administration as a lotion, gel or an emulsion or for oral administration as a dietary supplement or as a food ingredient. Also, the pharmaceutical composition may include a derivative or analog of the bioactive pentapeptide.

In general, in a third aspect, the invention relates to a food product comprising the bioactive pentapeptide of SEQ ID NO: 1 and a food substance. The food substance may take the form of: beverages, such as non-alcoholic and alcoholic drinks, soft drinks, sport drinks, energy drinks, fruit juices, lemonades, teas and milk-based drinks; dairy products, such as yogurts; and fortified foods, such as bakery items and as snacks, cereal-based foods and breakfast cereals.

In general, in a fourth aspect, the invention relates to a method of treatment or prevention of diseases, such as cancer, obesity or Alzheimer's. The method includes the steps of administering a therapeutically effective amount of a composition comprising the bioactive pentapeptide. The method of treatment or prevention of cancer may be for proliferation of human colon, liver, breast and/or lung cancer. The composition of the method may be administered topically as a lotion, gel or an emulsion or administered orally as a dietary supplement or as a food ingredient. In addition, the composition can be a pharmaceutical, nutraceutical or food composition.

In general, in a fifth aspect, the invention relates to the use of at least one bioactive pentapeptide comprising the amino acid sequence Glu-Gln-Arg-Pro-Arg (SEQ ID NO: 1) in the manufacture of a nutraceutical composition.

BRIEF DESCRIPTION OF THE DRAWINGS

FIG. 3 is a graphical representation of the viability of HepG2 cells exposed to rice bran peptide fractions measured by trypan blue dye exclusion assay. Values are means of two trials ±SE. Values not connected by same letters are significantly different ($P<0.05$). −ve control: saline with 0.1% methanol; and +ve control: Genistein (200 µM, 400 µM) in saline with 0.1% methanol;

FIG. 4 is a graphical representation of a MTS assay for the determination of the anti-cancer activities of GI-resistant, rice bran peptide fractions on Caco-2 and HepG2 cells. Values are means of two trials ±SE. Values not connected by same letters are significantly different ($P<0.05$), MTS-(3-(4,5-dimethylthiazole-2-yl)-5-(3-carboxymethoxyphenyl)-2-(4-sulfophenyl)-2H-tetrazolium. Negative: saline; and Positive: Genistein (200 µM);

In FIG. 19a, the glycos-peptides were prepared at varying RH at pH 6; in FIG. 19b, the glycos-peptides were prepared at varying RH at pH 7; and in FIG. 19c, the glycos-peptides were prepared at varying RH at pH 8. Peptide-glucose mixture samples were maintained at 45, 55, and 65 RH prepared at pH 6, 7 and 8 for 24 h. Plotted values are means with standard deviations;

Figure 1:
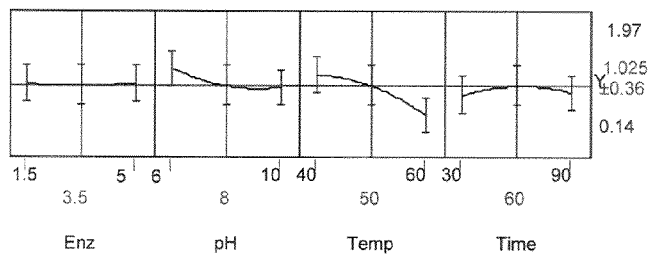
FIG. 1 is a Box-Behnken RSM 3 points prediction profiler selection of the optimum conditions needed for proteolytic digestion in accordance with an illustrative embodiment of the bioactive pentapeptides from rice bran and use thereof disclosed herein.

Other advantages and features will be apparent from the following description and from the claims.

DETAILED DESCRIPTION OF THE INVENTION

The compositions and methods discussed herein are merely illustrative of specific manners in which to make and use this invention and are not to be interpreted as limiting in scope.

While the compositions and methods have been described with a certain degree of particularity, it is to be noted that many variations and modifications may be made without departing from the spirit and scope of this disclosure. It is understood that the compositions and methods are not limited to the embodiments set forth herein for purposes of exemplification.

In general, the invention relates to bioactive proteins, peptides and enzymatic hydrolysates from rice bran and use thereof, and more particularly to a purified, unmodified and modified bioactive pentapeptide from heat stabilized defatted rice bran having anti-cancer, anti-obesity, anti-Alzheimer and other health-promoting activities. Additionally, the bioactive pentapeptide has a unique sequence that renders its bioactive nature, which can enhance glucose uptake into cells, act to sequester bad cholesterol and fatty acids accumulating in excessive BMI states and/or mitigate molecular events taking place in neuronal cells during the onset of Alzheimer's disease. In addition, the bioactive pentapeptide may be an effective anti-hypertensive, anti-mutagenic and anti-microbial agent.

The bioactive pentapeptide refers to a peptide having the amino acid sequence of Glu-Gln-Arg-Pro-Arg (EQRPR) (SEQ ID NO: 1) or a structural/functional variant thereof. The C-terminus end of the bioactive pentapeptide includes three (3) amino acids, Arg-Pro-Arg, with Glu-Gln amino acids in the N-terminus end. The bioactive pentapeptide of SEQ ID NO: 1 has an exact mass of 685.378 Da. The presence of charged (glutamic acid) and heterocyclic amino acid (proline) in the sequence of the bioactive pentapeptide may attribute to the health-promoting properties. A variant to the bioactive pentapeptide could be made by introducing mutations in SEQ ID NO: 1 at positions not essential to the health-promoting activities. Further, amino acid substitutions of replacing one amino acid residue with another having similar chemical properties is unlikely to affect the activity of a peptide, and such mutations is also expected to preserve the health-promoting activities of any structural variants of the bioactive pentapeptide. The health-promoting activities of the bioactive pentapeptide can be determined by assays described in the following examples. Furthermore, the bioactive pentapeptide can be isolated from a natural source, such as rice bran, produced by the expression of a recombinant nucleic acid molecule, or can be chemically synthesized.

A method for making the bioactive pentapeptide includes the: (1) preparation using food grade materials including alkali/acid and/or proteolytic enzymes and fermentation; and (2) separation of protein hydrolysates from heat stabilized defatted rice bran (HDRB) or non-defatted rice bran followed by generation of GI-resistant peptides, which are fractionated to obtain definite molecular sized fractions of the bioactive pentapeptide. When the rice bran is defatted and directly enzymatically hydrolyzing the high-quality protein using endoprotease, the method of making the bioactive pentapeptide disclosed herein sustainably releases peptides in a consistent manner.

Due to its excellent health-promoting activities in vitro, the bioactive pentapeptide, or functional/structural variant thereof, can be incorporated as an active ingredient into pharmaceutical, nutraceutical and food compositions for preventing or treating various cancer lines, obesity-related diseases and/or Alzheimer's disease, as well as acting as an anti-hypertensive, anti-mutagenic and/or anti-microbial agent. These compositions incorporating the bioactive pentapeptide may further contain protective hydrocolloids, such as gums, proteins, modified starches, binders, film forming agents, encapsulating agents/materials, wall/shell materials, matrix compounds, coatings, emulsifiers, foaming agents, surface active agents, solubilizing agents, e.g., oils, fats, waxes, lecithins etc., adsorbents, carriers, fillers, co-compounds, dispersing agents, wetting agents, processing aids (solvents), flowing agents, flavoring agents, sweetening agents, coloring agents, weighting agents, jellyfying agents, gel forming agents, anti-oxidants, anti-microbial and other preservative agents.

Moreover, a multi-vitamin and mineral supplement may be added to the compositions incorporating the bioactive pentapeptide to obtain an adequate amount of an essential nutrient, which is missing in some diets. The multi-vitamin and mineral supplement may also be useful for disease prevention and protection against nutritional losses and deficiencies due to lifestyle patterns. In addition, the compositions having the bioactive pentapeptide may be incorporated into beverages, e.g., non-alcoholic and alcoholic drinks, soft drinks, sport drinks, energy drinks, fruit juices, lemonades, teas and milk-based drinks, along with other dairy products and/or fortified food and bakery goods.

Further, the pharmaceutical, nutraceutical and food compositions may be in any galenic formulation that is suitable for administrating to the human body, especially in any form that is conventional for oral administration, e.g., in solid form such as (additives/supplements for) food or feed, food or feed premix, fortified food or feed, tablets, pills, granules, capsules, and effervescent formulations, such as powders and tablets, or in liquid form, such as solutions, emulsions or suspensions, e.g., beverages, pastes and oily suspensions. The pastes may be filled into hard or soft shell capsules, whereby the capsules feature, e.g., a matrix of (fish, swine, poultry, cow) gelatin, plant proteins or ligninsulfonate. Examples for other acceptable forms of administration are transdermal, parenteral and injectable. The pharmaceutical, nutraceutical and food compositions may be in the form of controlled immediate or sustained release formulations.

The bioactive pentapeptide provides a method for prophylactic or therapeutic treatment of various cancer lines in a patient by administering to the patient the bioactive pentapeptide, or a functional/structural variant thereof, at an amount effective for providing anti-cancer activity. In addition, the bioactive pentapeptide provides a method of prophylactic or therapeutic treatment of obesity and obesity-related diseases in a patient by administering to the patient the bioactive pentapeptide, or a functional/structural variant thereof, at an amount effective for providing anti-obesity activity. Moreover, the bioactive pentapeptide provides a method of prophylactic or therapeutic treatment of Alzheimer's in a patient by administering to the patient the bioactive pentapeptide, or a functional/structural variant thereof, at an amount effective for providing anti-Alzheimer's disease activity. It is understood that the actual amount of the bioactive pentapeptide to be administered can vary in accordance with the age, size, condition and other factors associated with the specific patient to be treated, depending upon the discretion of medical professionals.

The bioactive pentapeptide from rice bran and use thereof disclosed herein is further illustrated by the following examples, which are provided for the purpose of demonstration rather than limitation.

Materials and Methods

Isolation of Protein Hydrolysates Having Anti-Cancer Properties from Heat-Stabilized Defatted Rice Bran Rice bran, an economical, under-utilized co-product of rough rice milling was used to produce peptide hydrolysates, which were investigated for various health-promoting activities. Protein hydrolysates prepared by Alcalase hydrolysis under optimized conditions were treated further to obtain gastrointestinal resistant peptide hydrolysates, which were fractionated into >50 kDa, 10-50 kDa, 5-10 kDa and <5 kDa sizes, and evaluated for inhibitory activity on proliferation of human colon (Caco-2; HCT-116), liver (HepG2), breast (MCF-7; HTB-26) and lung (NCI-H1299) epithelial cancer cell lines by trypan blue dye exclusion assay. By way of example, GI resistant <5 kDa and 5-10 kDa sized peptide fractions inhibited growth of Caco-2 cells by 80% and <5 kDa fraction inhibited growth of HepG2 cells by ~50% compared to controls and non-resistant fractions. An MTS cell titer assay confirmed anti-proliferative effects of the peptide fractions. The results demonstrated that 5-10 kDa and <5 kDa sized GI resistant fractions promoted significant ($p<0.05$) inhibitory activities on cancer cell lines compared to controls.

Materials. HDRB was obtained from Riceland Foods (Stuttgart, Ark.), the Romicon ultrafiltration system from Koch Membrane Systems (Massachusetts, USA), and food-grade Alcalase enzyme from a bacterial strain purchased from Novozyme (North Carolina, USA). Human colon (Caco-2; HCT-116), liver (HepG-2), breast (HTB-26) and lung (NCI-H1299) epithelial cancer cell lines were purchased from ATCC (Manassas, Va.). Dulbecco's modified Eagle's medium, fetal bovine serum and gentamycin were purchased from Hyclone (Logan, Utah). MTS kits were purchased from Promega (Madison, Wis.). Hp 1090 series, HPLC system, reverse-phase C-18 peptide column, analytical grade, sephadex G-75 resin from Pharmacia Biotech AB (Uppsala, Sweden), biopore C18 preparative HPLC column, amino acid analyzer from Beckman Coulter, Bruker Reflex III (Bruker Daltonics GMBH, Bremen, Germany) and Bruker Ultraflex II time-of-flight mass spectrometers at the Statewide Mass Spectrometry Facility, University of Arkansas. All other chemicals purchased were of HPLC grade and purchased from Sigma-Aldrich Corp. (St. Louis, Mo.).

Enzymatic Hydrolysis of HDRB to Obtain Protein Hydrolysates: Approximately 500 g of ground and sieved HDRB (passed through a 60 mesh) was dissolved and homogenized with 0.6 L deionized water and stirred for 30 min at room temperature. Based on a response surface method optimization design, HDRB was digested with 3.5 AU (Anson units of enzyme) Alcalase (4970 µL) at pH 8.0 and heated at 50° C. for 60 min. To arrest proteolytic digestion, the enzyme was inactivated by heating the suspension at 85° C. for 3 min. The hydrolysis mixture was centrifuged at 3,000 g for 15 min to obtain the hydrolysates in the supernatant. The supernatant was freeze-dried and stored at 4° C. until needed.

Degree of Hydrolysis. The degree of hydrolysis was determined according to the OPA method using serine as standard. The sample solution was prepared by dissolving approximately 0.1 g to approximately 1.0 g of freeze-dried hydrolysate in 100 mL of deionized water. Serine standard/sample solution (400 μL) was added to the test tube (time 0) containing 3 mL of OPA reagent, mixed for 5 s, and allowed to stand for 2 min, and then the absorbance was read at 340 nm in the spectrophotometer.

The degree of hydrolysis was calculated as follows: $DH = h/h_{tot} \times 100\%$, where $h$ is the number of cleaved peptide bonds and $h_{tot}$ is the total number of peptide bonds per protein calculated as $h_{tot} = (\text{serine-NH}_2 - 0.4)$, where serine-NH$_2$ is the meqv of serine NH$_2$ per gram of protein.

$$\text{Serine-NH}_2 = \frac{(OD_{sample} - OD_{blank}) \times 0.9516 \ meqv/L \times (\text{sample volume in } L) \times 100/(\text{sample wt in g} \times \text{protein \%})}{(OD_{standard} - OD_{blank})}$$

Protein Content. Protein contents were determined according to the Kjeldahl method. A Kjeldahl 2006 Digester (Foss Tecator, Hoganas, Sweden) was used to digest samples.

Generating GI Juices Resistant Bran Hydrolysates. It is essential that the peptides be resistant to the GI tract to impart uninhibited biological function and bioavailability. Hence, the bran hydrolysates were passed through a simulated gastric and intestinal solution as described below.

Simulated gastric juice was prepared as follows: To deionized water (90 mL) in a 100 mL volumetric flask were added sodium chloride (0.2 g) and concentrated hydrochloric acid (0.7 mL) and stirred for 30 min. The final volume was made up to 100 mL with deionized water and transferred into a beaker. The pH was adjusted to 2.0. Purified enzyme pepsin (0.32 g) was added and stirred. The temperature of the solution was maintained at 37° C. Five grams (5 g) of freeze-dried hydrolysate was dissolved in the simulated gastric juice and allowed to incubate at 37° C. with constant shaking. After 120 min, the pH was adjusted to 7.2 to inactivate the enzyme. The reaction mixture was centrifuged at 3000 g for 20 min to obtain soluble peptide hydrolysates in the supernatant. In the in vitro digestibility studies, the samples were typically examined up to 120 min. The resistant supernatant hydrolysate was freeze-dried and stored at 4° C.

Simulated intestinal juice was prepared as follows: To deionized water (90 mL) in a 100 mL volumetric flask were added potassium phosphate monobasic (0.68 g) and sodium hydroxide 0.2 N (7.7 mL) and stirred for 30 min. Final volume was made up to 100 mL and transferred into a beaker. The pH of the solution was adjusted to 8.0, and the mixture was maintained at 37° C. Pancreatin at a final concentration of 0.1% was added and stirred. The simulated gastric juice treated hydrolysate (in freeze-dried form) was dissolved in the simulated intestinal juice and allowed to incubate at 37° C. with constant shaking. After 120 min, the enzyme was inactivated by heating at 85° C. for 10 min. The reaction mixture was then centrifuged at 3000 g for 20 min to obtain soluble peptide hydrolysate in the supernatant. The hydrolysate was stored at 4° C.

Fractionation of GI-Resistant Peptide Hydrolysates by Ultrafiltration. Fractionation was carried out with a Romicon ultrafiltration system equipped with 1 in. diameter, hollow-fiber polysulfone membrane cartridges. Approximately 500 mL of filtered soluble GI-resistant peptide hydrolysate were run through sequential ultrafiltration columns with membrane cartridges having nominal molecular weight cutoffs (MWCO) of 50, 10, and 5 kDa. Approximately one third of the volume of the hydrolysate was ultrafiltered through each membrane as retentates and the rest as permeates. In particular, in each MWCO cartridge, the peptide hydrolysate was ultrafiltered at a dilution factor of 5. Immediately after the first ultrafiltration, the retentate was diafiltered twice with 2 volumes of deionized water. The permeates of the first (50 kDa) ultrafiltration and the second diafiltration step were pooled and subjected to the second run through the 10 kDa and then the 5 kDa MWCO's, respectively. The resulting retentates from each of the MWCO were freeze-dried and stored at 4° C. Only GI-resistant peptide hydrolysates were subjected to fractionation and only of those being <5 kDa were tested for inhibitory activity against human colon, liver, lung and breast cancer cell lines.

Human Cancer Cell Cultures. Human colon epithelial cancer cell line Caco-2, liver epithelial cancer cell line HepG2 and breast epithelial cancer cell line HTB-26 were cultured separately at 37° C. in Dulbecco's Modified Eagles Medium (DMEM) in the presence of 10% fetal bovine serum, supplemented with 1 mM L-glutamine, sodium pyruvate, 1 mM sodium bicarbonate, and 50 μg/mL gentamycin. Human lung epithelial cancer cell line NCI-H1299 was cultured in RPMI-1640 medium supplemented with 10% fetal bovine serum. After cell growth reached 70%, cell viability was monitored by employing the trypan blue dye exclusion assay after peptide treatments. Briefly, the monolayer was allowed to grow for 2-3 days at 37° C. on 24-well flat-bottom plates. One hundred microliters (100 μL) of rice bran peptide fractions at 1 mg/mL protein content was added to the cultures. For positive control genistein at 200 and 400 μM in saline and for negative control saline alone was used. After 24-48 h of treatments, the medium was removed, and the cells were briefly dissociated with 0.1% trypsin and 0.53 mM ethylenediaminetetraacetic acid (EDTA) solution. Following this, 0.5% trypan blue dye mixed in growth medium was added to each well. Samples were then aspirated from each well and loaded onto chambers in a hemocytometer cell, and cell counts were taken. This assay reflected the number of viable cells that survived after treatment with peptide samples.

Human colon cancer cell line HCT-116 was grown in McCoy's 5a medium supplemented with 10% fetal bovine serum and 100 μg/mL of penicillin and streptomycin (GIBCO-BRL). Human breast (HTB-26) cancer cell line was cultured separately at 37° C. in DMEM in the presence of 10% fetal bovine serum, supplemented with 1 mM L-glutamine, sodium pyruvate, 1 mM sodium bicarbonate and 50 μg/mL gentamycin. Cells were grown at 37° C. under a humidified atmosphere of 5% carbon dioxide. Based on the results from the Caco-2 and HepG2 studies, the <5 kDa peptide fraction was used because of its ability to inhibit growth of cancer cells. Hence <5 kDa peptide fraction was selected for testing against HCT-116 and HTB-26 cell lines. After cell growth achieved 70%, they were treated with different concentrations of bran peptide fraction <5 kDa for different time periods and evaluated for growth inhibition properties.

MTS and MTT Assay. Cell proliferation inhibition was determined using the phenazine methosulfate 3-(4,5-dimethyl thiazole-2-yl)-2,5-diphenyl tetrazolium bromide (MTS) mix-based cell titer assay and the [3-(4,5-dimethyl thiazole-2-yl)]-2,5-diphenyl tetrazolium bromide (MTT)-based cell titer assay. After about 36 h of Caco-2, HepG2, HCT-116, HTB-26 and NCI-H1299 cell growth, respectively, cells were trypsinized, loaded onto a hemocytometer, and counted.

Approximately 1000 cells per well was used for growth onto 96-well flat-bottom plates. The cells were allowed to attach and grow for 36 h. After 36 h, old medium was replaced with fresh medium, and samples of rice bran peptide fractions were treated with the cells for determining the effect on growth as a concentration- and time-dependent manner. After 2-4 h of exposure of the rice bran peptides to the monolayer, the MTS mix was added at a final volume of 20 µL/100 µL of medium and then incubated for an additional 60 min under the same conditions. MTT dye was added after each time-point followed by the termination of the formation of colored formazan product by a detergent solution. The reaction was terminated by adding 10% SDS, and the absorbance of formazan was measured at 490 and 570 nm in a Tunable Versamax Microplate Reader (Molecular Devices, Sunnyvale, Calif.). Positive and negative controls were used similarly as used in the trypan blue dye exclusion assay, including appropriate row or column of wells was left untreated at each time-point. All assays were performed in duplicates, and the results are expressed as mean values ±standard error.

Clonogenic Assay. To determine the anti-cancer activity of rice bran peptides, a clonogenic cytotoxicity assay was performed to test the efficacy of rice bran peptides on proliferating cancer cells. The clonogenic assay was performed using the HCT-116 cell line. Cells were trypsinized and a single cell suspension was prepared. Cells were plated at a density of 100 cells per 35 mm well. Cells were treated with different concentrations of the rice bran peptide fraction. After 72 h, the medium was replaced with fresh medium. Cells were allowed to grow for another 8 days and then stained with 0.025% crystal violet. The excess crystal violet was removed with 30% methanol, plates were air dried at room temperature, and numbers of colonies were counted.

Data Analysis. Experimental data from the Caco-2 and HepG2 cell cultures were analyzed using JMP 7.0 statistical software with the least significant differences between samples being $P<0.05$, and experimental data from the HCT-116, HTB-26 and NCI-H1299 cell growths were analyzed using SigmaPlot statistical software (Systat Software, Inc., San Jose, Calif.) with sample means and standard errors of approximately 10%. Response surface method was used as a model to optimize enzymatic hydrolysis of rice bran using Alcalase enzyme.

EXAMPLE 1

Enzymatic Hydrolysis of Rice Bran by Alcalase Enzyme and Protein Contents

A four-factorial response surface design optimization with optimum degree of hydrolysis as well as digested protein contents as response values were determined. The four parameters, enzyme concentrations [1.5, 3.5 and 5 Alcalase units (AU)], pH (6, 8, and 10), temperature (40, 50, and 60° C.), and incubation time for digestion (30, 60, and 90 min), were fitted to generate optimum concentrations of enzyme, pH, time and temperature for achieving optimum degree of hydrolysis. Box-Behnken surface response using the JMP 7.0 statistical software was used to evaluate the interactions between parameters to generate optimum values for enzymatic hydrolysis. A degree of hydrolysis at 23.4% was considered to be optimum, with an E/S ratio of 0.01.

Digested protein contents (in mg/mL) were obtained for each factorial combination. For example, at 1.5 AU enzyme concentration, pH 8, and 40° C. for 60 min of digestion the digested protein content was found to be 0.993 mg. The prediction profile from the response surface design shown in FIG. 1 enabled selection of the optimum conditions needed for proteolytic digestion. The prediction profile designated 3.5 AU enzyme concentration at pH 8.0, 50° C., and 60 min time of digestion for obtaining the optimum value for digested protein content, 1.025±0.36 mg/mL, with a DH of 23.4%. For consistent production of peptides from rice bran, optimized conditions were used for performing enzymatic hydrolysis.

EXAMPLE 2

Colon and Liver Anti-Cancer Activity Evaluation of GI-Resistant and Nonresistant Rice Bran Peptide Hydrolysate Fractions The trypan blue dye exclusion assay was conducted to determine cell viability after treatment of cells with peptide fractions. This assay evaluates the number of viable cells that remain after exposure of peptides on to Caco-2 as well as HepG2 cells. Both GI resistant peptides as well as non-GI resistant peptides were tested on colon and liver cancer cell lines.

Figure 2:
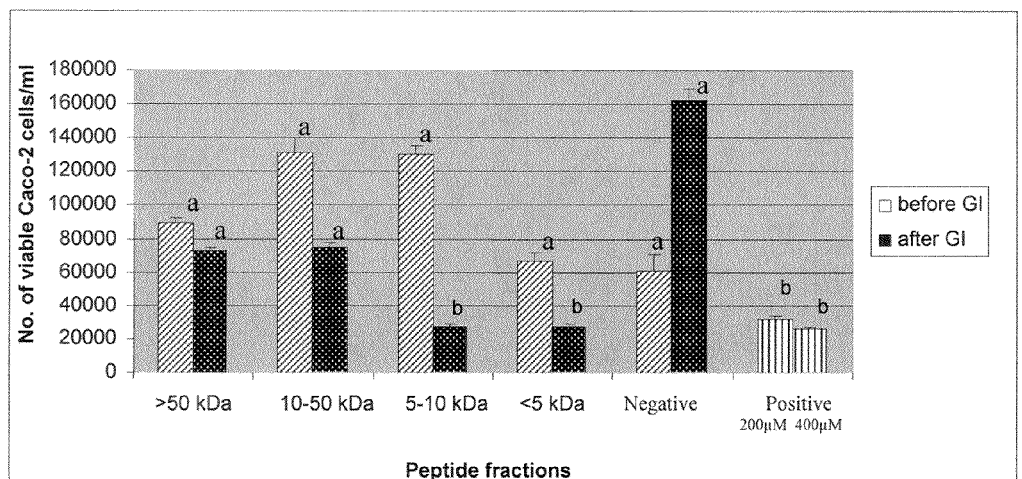
FIG. 2 is a graphical representation of the viability of Caco-2 cells after exposure to rice bran peptide fractions measured by trypan blue dye exclusion assay. Values are means of two trials ±SE. Values not connected by same letters are significantly different ($P<0.05$). −ve control: saline; and +ve control: Genistein (200 µM, 400 µM)

FIG. 2 depicts the effect of GI and non-GI resistant peptide fractions on Caco-2 cells. On Caco-2 cells, GI-resistant peptide fractions of sizes <5 and 5-10 kDa were found to significantly inhibit the proliferation of viable cells compared to higher molecular weight fractions (>10 and >50 kDa), non-GI resistant fractions and negative control. There was an approximately 3-fold reduction in viable cells between GI-resistant and non-GI resistant fractions that were below 10 kDa. Similar patterns of inhibition between fractions that were above 10 kDa were not observed. The positive control used was genistein at concentrations of 200 and 400 µM. Genistein is an isoflavone that is a known anticancer agent. At 200 µM concentration, there were 20000 viable cells/mL on Caco-2 cell line, which was significantly less than the negative control (lacking genistein) that resulted in over 100000 viable cells/mL.

FIG. 3 depicts the effect of GI- and non-GI-resistant peptide fractions on HepG-2 cells. On HepG-2 cells, GI-resistant peptide fraction <5 kDa was alone shown to inhibit proliferation of viable cells significantly compared to non-GI-resistant fraction and negative control. From experimental data, it was found that the resistant fractions were more bioactive than the nonresistant fractions. When the peptide fractions were tested for GI resistance, resistant peptides were generated, which not only meant that they were exposed to highly specific enzymatic cleavage, causing them to expose more side chains, but also may imply their suitability in the digestive tract, rendering absorptive and hence consumable properties. In the human body, peptides are usually generated when proteins pass through the intestine, where gastrointestinal enzymes act and release the peptides, before absorption. Depending upon the nature of the proteins, peptides, and their amino acid sequences, these proteins/peptides may exert specific biological functions. Bioactive peptides when ingested should pass through the intestinal barrier and be transported to the target organs to impart anti-hypertensive, anti-cancer or other health-promoting activities. Thus, gastrointestinal resistant peptide fractions (<5 and 5-10 kDa) tend to open their bioactive groups, imparting more bioactivity by effectively inhibiting proliferation of both colon and liver cancer cells more than the nonresistant fractions. Moreover, only soluble peptides were generated in a process of eliminating organic or other constituents of rice bran that could possibly interfere with bioactivity. While rice bran has organic bioactive components, soluble peptides derived from enzymatic hydrolysis of protein hydrolysates can aid in inhibitory action of human anti-colon and liver cancer cell proliferation and can have true biological activity in terms of bioavailability and delivery.

To confirm the findings of peptide bioactivity, a more specific assay, the MTS-based titer assay, was conducted. FIG. 4 depicts MTS-based cell titer assay results for confirming inhibitory actions of peptide fractions on colon and liver cancer cells, respectively. This assay reflects cytotoxicity as an indication of early damage to cells thereby reducing metabolic (mitochondrial) activity. There is >80% cytotoxicity to HepG2 cells with the <5 kDa fraction and nearly 70% cytotoxicity to Caco-2 cells. The 5-10 kDa fraction caused 60% cytotoxicity to HepG2 cells and 50% cytotoxicity to Caco-2 cells. These results confirm that resistant peptide fractions <5 and 5-10 kDa inhibit growth of colon and liver cancer cells more effectively than the nonresistant fractions. For fractions that were >10 kDa pronounced bioactivity was not observed, possibly because the fractions are longer in length requiring more time of proteolytic exposure to unfold. Since the trypan blue dye exclusion assay was enumerative of the cell viability after peptide treatments showing significant bioactivities with the GI-resistant fractions, only GI-resistant fractions were subjected to the MTS assay.

EXAMPLE 3

Figure 5:
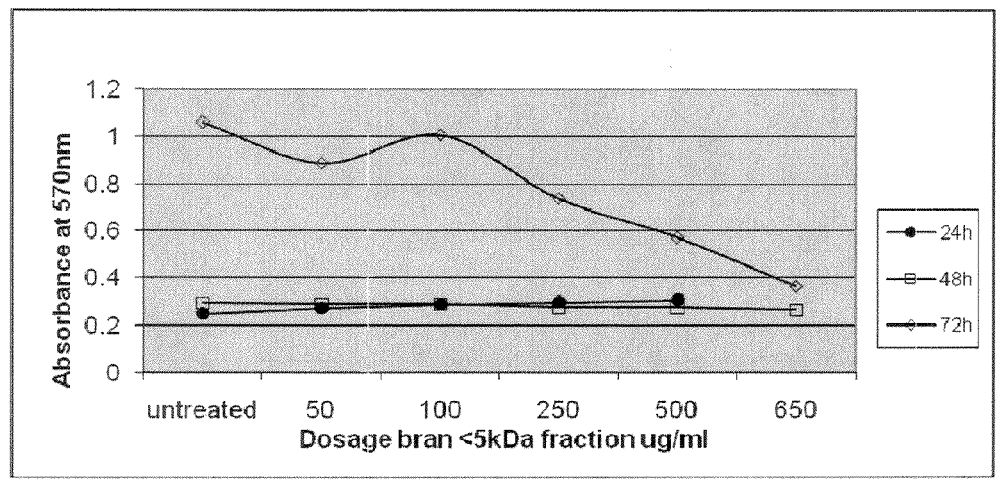
FIG. 5 is a graphical representation of a MTS assay for the determination of the anti-cancer activities of the bioactive pentapeptides from rice bran peptide <5 kDa fractions (GI-resistant fractions) on HCT-116 cells.
Figure 6:
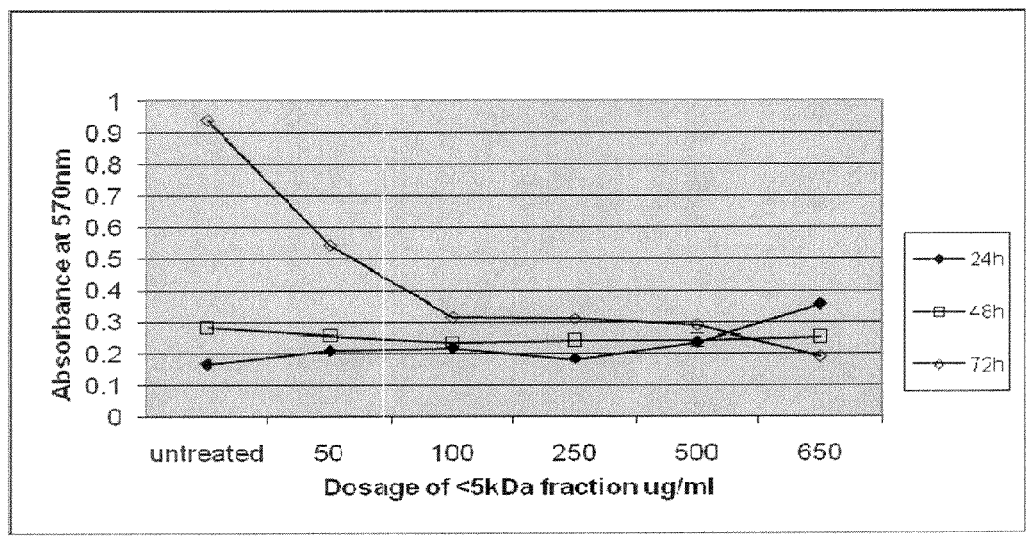
FIG. 6 is a graphical representation of a MTS assay for the determination of the anti-cancer activities of the bioactive pentapeptides from rice bran peptide <5 kDa fractions (GI-resistant fractions) on HTB-26 cells.

Colon and Breast Ant-Cancer Activity Evaluation of GI-Resistant and Nonresistant Rice Bran Peptide Hydrolysate Fractions Treatment with rice bran <5 kDa fraction at 24 and 48 h time-points revealed no inhibition in the growth of HCT-116 colon cancer cells compared to the untreated cells, whereas at the 72 h time-point there was a dose- and time-dependent inhibition in the growth of HCT-116 cells (FIG. 5). The growth of HCT-116 cells was reduced by nearly 80% after the treatment with 650 g/mL of the <5 kDa fraction at the 72 h time-point. Similar results were obtained with HTB-26 breast cancer cells. Treatment with rice bran <5 kDa fraction at 24 and 48 h time-points showed no inhibition compared to the untreated cells. At the 72 h time-point, however, there was a significant inhibition in the growth of HTB-26 cells in a dose- and time-dependent manner (FIG. 6). Like HCT-116 cells, the HTB-26 cells also showed maximum sensitivity at 650 g/mL of <5 kDa fraction treatment with a 65% inhibition in the growth at 72 h time-point. As noted above, >50, 10-50 and 5-10 kDa fractions revealed no growth inhibitory effect on colon and liver cancer cells, however, the growth inhibitory activity for colon and breast cancer cells of rice bran peptide is present in the <5 kDa fraction.

Figure 7:
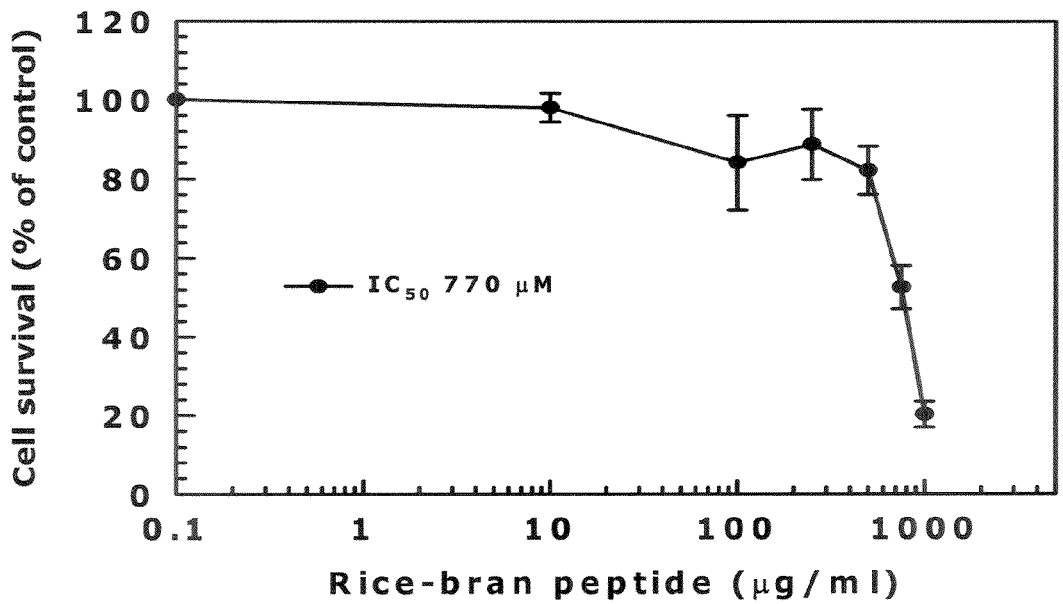
FIG. 7 is a graphical representation of a clonogenic toxicity assay of the bioactive pentapeptides from rice bran peptide <5 kDa fractions (GI-resistant fractions) on HCT-116 cells.
Figure 8:
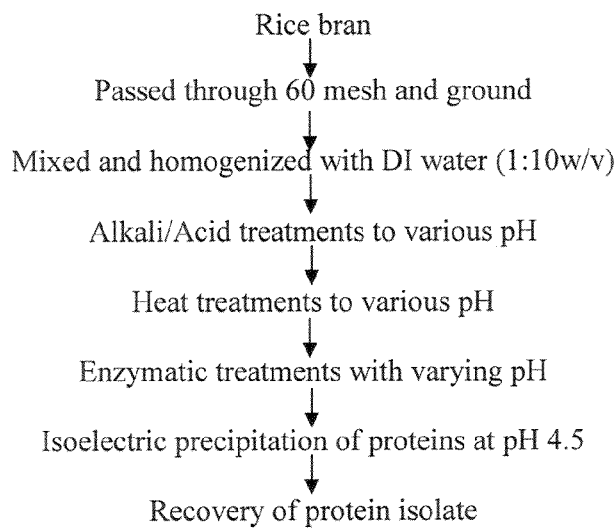
FIG. 8 is a process flow chart illustrating an example of the steps involved towards the preparation of rice bran peptide fractions in accordance with an illustrative embodiment of the bioactive pentapeptides from rice bran and use thereof disclosed herein.

The clonogenic assay also indicates the toxicity of the <5 kDa fraction to HCT-116 cells (FIG. 7). The cytotoxicity of the <5 kDa fraction was pronounced after treating the cells with 500 g/mL and that the IC50 dose of the <5 kDa fraction was 770 g/mL. These results indicate that <5 kDa peptide fraction of the rice bran has a potent anti-tumor activity for colon cancer cells.

As discussed, the screening for determination of anti-cancer activity was done employing the MTT assay and subsequently confirmed by clonogenic assay on the anti-cancer fraction. The time- and concentration-dependent growth inhibition patterns observed with the <5 kDa peptide fraction on HCT-116 and HTB-26 reveal better results with HCT-116 cells by the MTT assay. This suggests that the fraction could have a better and positive impact on reducing progression of human colon cancer. Further, the clonogenic assay, which also reflects cytotoxicity confirms that a higher dosage and longer time is needed for the <5 kDa fraction to have strong inhibitory or cytotoxicity effect on the growth of especially the colon cancer cells. Since <5 kDa fraction showed a better inhibition on colon cancer cells compared to liver cancer cells, clonogenic assay of the <5 kDa fraction was done only on colon cancer cells. The dosage and time-dependent growth inhibition pattern may imply that the fractions may be a slow-acting. Higher doses may reduce the time needed for killing the maximum number of cells.

Bioactive Pentapeptide from Heal Stabilized Detailed Rice Bran

Based on the above findings that rice bran peptide fractions have the ability to cause growth arrest in colon, breast, lung and liver cancer cell types in vitro, the <5 kDa fraction originally separated by pressure-driven membrane based separation (ultrafiltration) that showed significant anti-cancer effects was subjected to further characterization to yield pure peptide(s) having similar or enhanced anti-cancer properties.

Purification by IEC followed by reverse phase HPLC was done to obtain single pure peptide(s) from the >5 kDa fraction. Fifty millimolar (50 mM) sodium chloride eluate from ion exchange column caused approximately 75% inhibition to colon and liver cancer cells growth and, 60% and 68% inhibitory activities on lung and breast cancer cells, respectively. The eluate was purified using HPLC using peptide-specific column. It was observed that the 60-70 min peak showed enhanced anti-cancer activity, namely, 84% inhibition on colon, 80% on breast and 84% on liver cancer cells. Accurate molecular mass of the pure peptide by MALDI-TOF revealed a mass of 685.378 Da. Amino acid analysis revealed the presence of Glutamic acid, Proline and Arginine. Tandem mass spectrometry for determining the amino acid sequence of the pure peptide(s) was done using post-source decay fragmentation analysis. The sequence of the bioactive pentapeptide from the rice bran is Glu-Gln-Arg-Pro-Arg (EQRPR) (SEQ ID NO: 1).

Ion Exchange Chromatography: A sephadex G-75 ion exchange resin was packed into a glass column and equilibrated with 10 mM phosphate buffer, pH 8.0. Ten milliliters (10 mL) of <5 kDa peptide hydrolysate (~1 mg/mL protein concentration) was loaded onto the column at 1 mL/min flow rate. The elution was started by washing the unbound hydrolysate eluted with 10 mM phosphate buffer until about 5 bed volumes. After washing, the hydrolysate was eluted using 10 mM phosphate buffer containing 50 mM NaCl followed by elution with 10 mM phosphate buffer containing 100 mM NaCl for a total 5 bed volumes. The eluates were collected, concentrated in an Amicon concentrator with buffer exchange and stored at 4° C. The anti-cancer activity of the eluates obtained after ion-exchange was determined using the MTS assay described above.

Preparative HPLC Purification of IEC Eluate Showing Anti-Cancer Activity: Preparative scale peptide-specific column (Biopore Prep ID 22×L 250 mm part #34955) was used to separate peptides from the IEC eluates that showed better anti-cancer activity and the absorbance of the eluate monitored at 215 nm. The gradient from solvent A (1.2 ml TFA/ 1000 ml deionized water) to solvent B (0.1% TFA in Acetonitrile:water 50:50) was varied from 100% solvent A to 100% solvent B over 80 min at 2 ml/min flow rate monitored at 215 nm. The peaks were collected and tested for anti-cancer activity, and the peak that showed anti-cancer activity was fully characterized using mass spectrometry and amino acid sequencing.

Amino Acid Analysis: A modified method of AOAC 982.30a (1990) was used for hydrolyzing purified peptides. Ten milligrams (10 mg) of peptide samples were hydrolyzed in 10 mL of 6.0 N HCl under vacuum at 150° C. for 12 h and evaporated under nitrogen at 60° C. Sodium diluent buffer pH 2.2 (1 mL) was added to the dried peptide, filtered and the filtrate was analyzed for amino acids. The peptides were pretreated with performic acid prior to hydrolysis to preserve cysteine and methionine, while alkali hydrolysis was conducted to determine tryptophan (AOAC 982.15, 2000). Amino acid analysis of the filtrate was conducted on an automated amino acid analyzer (Beckman 6300, Beckman Instruments, Inc., Palo Alto, Calif.) at a flow rate of 0.67 mL/min (0.44 mL/min for buffer solutions and 0.23 mL/min for ninhydrin solution). Sodium citrate buffers (pH 3.3, 4.3 and 6.3) were used as eluents. The amino acid contents (in g/100 g sample) were quantified by comparing them with amino acid profiles from external amino acid standards as follows:

$$(Peak_{sample}/Peak_{standard}) \times Concentration_{standard} \times MW_{standard}$$

Mass Spectrometry Characterization of Pure Pentapeptide: For preliminary intact mass determination, 1.0 µl of the HPLC purified pentapeptide was mixed with 1.0 µl saturated HCCA and spotted on Bruker MTP 384 ground stainless steel MALDI target. Matrix assisted laser desorption ionization time of flight mass spectrometry (MALDI-TOF-MS) were acquired on a Bruker Reflex III and Bruker Ultraflex II time-of-flight mass spectrometers operated in the positive-ion reflectron mode. High resolution exact mass of the same peptide was obtained by using MALDI Ionspec 9.4 T Ion Cyclotron Resonance (MALDI-ICR) mass spectrometer. For the exact mass measurements, 2,5 dihydrobenzoic acid (DNB) was used as the MALDI matrix and followed exactly the same spotting technique.

MALDI Fragmentation: Fragmentation of intact peptide ions were performed to obtain sequence information using MALDI post source decay studies (MALDI-PSD). MALDI-PSD fragmentations of these ions were analyzed using the "Lift" mode in Bruker Ultraflex II MALDI-TOF-MS.

Data Analysis and de novo Sequencing: Fragmentation pattern obtained by MALDI-TOF-MS was interpreted using Bruker Biotools software, which uses de novo sequencing algorithm to determine the best sequence for the observed fragmentation pattern.

EXAMPLE 4

Anti-Cancer Activity of Eluates

Figure 9:
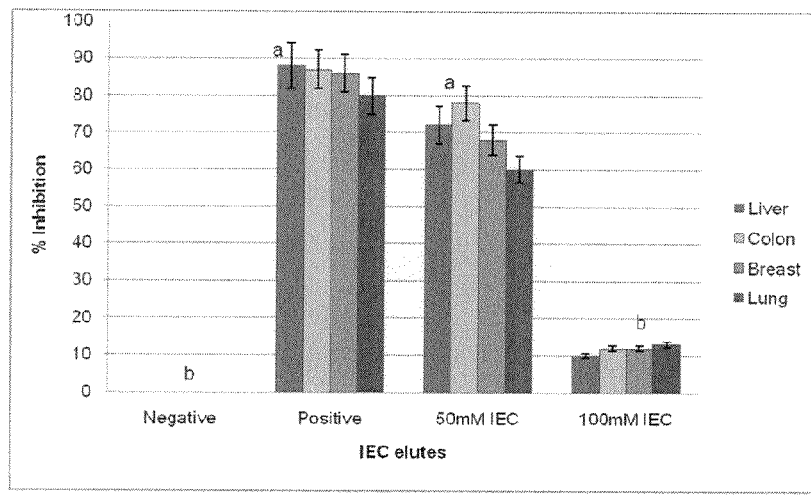
FIG. 9 is a graphical representation of a MTS assay for the determination of the anti-cancer activities of ion exchange chromatography (IEC) eluted fractions of the bioactive pentapeptides from rice bran disclosed herein. 100 mM: 100 mM NaCl eluate; 50 mM: 50 mM NaCl eluate. Values are means trials ±SE. Values not connected by same letters are significantly different ($P<0.05$), MTS-(3-(4,5-dimethylthiazole-2-yl)-5-(3-carboxymethoxyphenyl)-2-(4-sulfophenyl)-2H-tetrazolium. Negative (viability control): saline; and Positive (inhibitory control): Genistein (400 µg/ml)

On colon and liver cancer cells, the 50 mM NaCl eluate showed around 75% inhibition by the MTS dye assay. On breast cancer cells, there was 68% inhibition, while on lung cancer cells there was 60% inhibition (FIG. 9). While the 50 mM eluate showed cancer cell inhibitions better than the 100 mM eluates, the 50 mM eluate possibly had the pool of <5 kDa peptides that contribute towards the anti-cancer effect. The 50 mM IEC eluate was subjected to HPLC purification using a peptide-specific column.

Figure 10:
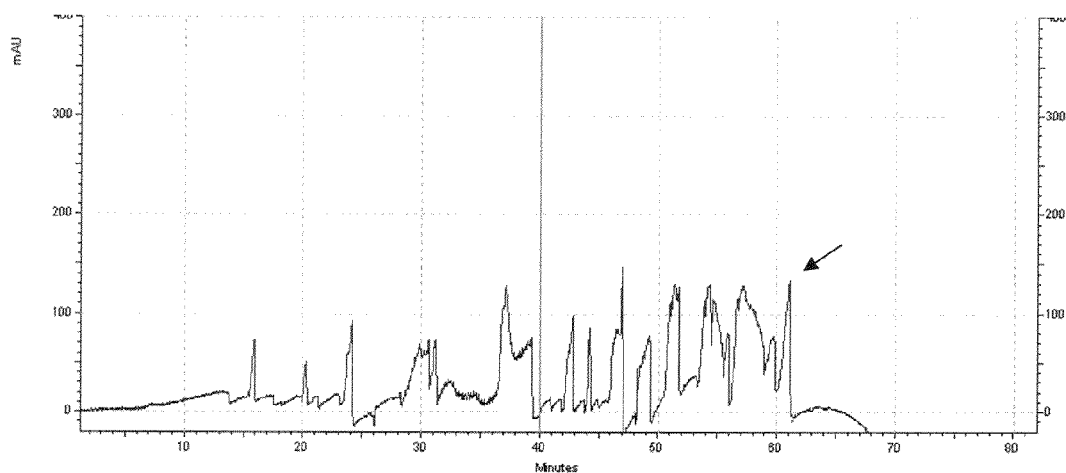
FIG. 10 is a HPLC profile of 50 mM IEC eluate from IEC. Peaks were collected every 10 min of the run and analyzed for anti-cancer activity. The 60-70 min peak (arrowhead) showed anti-cancer activity, which was further purified.
Figure 11:
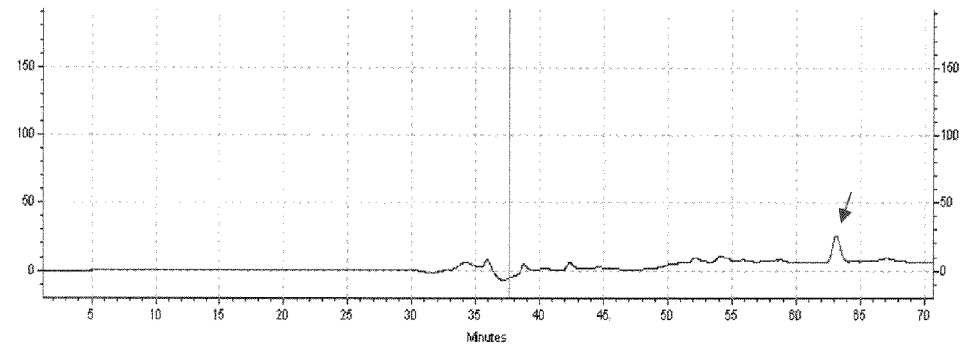
FIG. 11 is a HPLC profile of a purified, single peptide from 60-70 min fraction from IEC, and the 62 min peak (arrowhead) was collected for evaluation of anti-cancer effect.

FIG. 10 shows the HPLC profile of 50 mM IEC eluates. The peaks were collected at 10 min intervals and tested for anti-cancer activity. It was found that the 60-70 min fraction showed anti-cancer activity and this fraction was further purified in HPLC. FIG. 11 shows the purification of a single peptide obtained from 60-70 min fraction isolated from ion exchange chromatography. The peak eluted at 62 min was evaluated for anti-cancer activity and suggests the presence of both polar and non-polar amino acids that make up the peptide.

EXAMPLE 5

Anti-Cancer Activity of Pure Peptide

Figure 12:
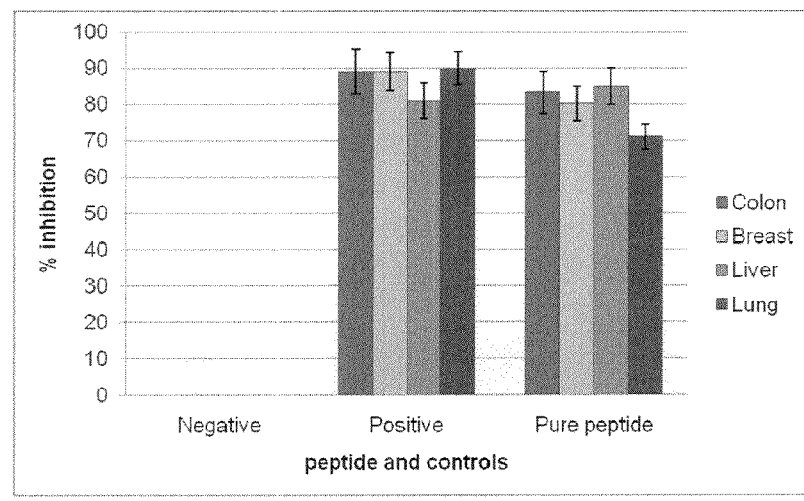
FIG. 12 is a graphical representation of a MTS assay for the determination of the anti-cancer activities of a purified bioactive pentapeptide from rice bran peptide <5 kDa fractions in accordance with an illustrative embodiment of the bioactive pentapeptides from rice bran and use thereof disclosed herein. Values are means trials ±SE. Values not connected by same letters are significantly different (P<0.05), MTS-(3-(4,5-dimethylthiazole-2-yl)-5-(3-carboxymethoxyphenyl)-2-(4-sulfophenyl)-2H-tetrazolium. Negative (viability control): saline; Positive (inhibitory control): Genistein (400 μg/ml); and Peptide fractions 1 mg/ml.

The pure peptide showed 84% inhibition on colon cancer cells, 80% on breast cancer cells and 84% on liver cancer cells, very similar to the positive (inhibitory) control (genistein) at 400 µg/ml. On breast and liver cancer cells, the pure peptide showed 80% and 85% inhibitions respectively, while on lung cancer cells there was 69% inhibition (FIG. 12). The results show that the peptide bears strong anti-cancer activities better than the <5 kDa peptide fraction from which it was purified. The purification of a single peptide from the <5 kDa rice bran hydrolysate resulted in identifying the anti-cancer component within rice bran. When its activity is tested and compared against all cancer types, enhanced activity of the peptide towards lung cancer cells was not demonstrated, however, more specific lung cancer types like small cell, squamous cell, and non-small cell lung cancer carcinomas may provide better inhibition of proliferation.

EXAMPLE 6

Bioactive Pentapeptide

Amino acid analysis revealed the predominance of three (3) amino acids suggesting the anti-cancer peptide could be a short peptide. As can be seen below in Table 1, the amino acid analysis of the pure peptide obtained after HPLC purification identified were arginine, proline, glutamic acid and glutamine.

TABLE 1

| Amino acids | Peptide nmol/ml |
| --- | --- |
| Glutamic Acid | 1.50 |
| Proline | 0.99 |
| Arginine | 2.65 |

Figure 13:
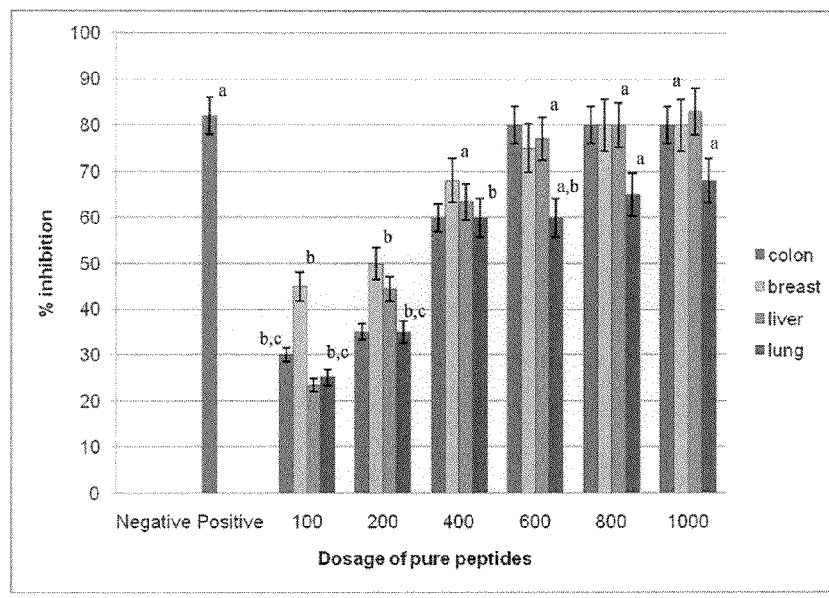
FIG. 13 is a graphical representation of a dose response at 24 h of the purified bioactive pentapeptide on various lines of human cancer cells. Values are means trials ±SE. Values not connected by same letters are significantly different (P<0.05), MTS-(3-(4,5-dimethylthiazole-2-yl)-5-(3-carboxymethoxyphenyl)-2-(4-sulfophenyl)-2H-tetrazolium. Negative (viability control): saline; and Positive (inhibitory control): Genistein (400 μg/ml)

Dose-response pattern of the pure peptide (FIG. 13) revealed that from 600 µg/mL to 1000 µg/mL maximum inhibition was achieved on most cancer cells even at 24 h period. There is an increase in inhibition pattern as the dosage increases and seems to plateau off beyond 600 µg/mL. The dosage for the pure peptide is similar to what was observed with the <5 kDa fraction on most cancer cell lines as per the earlier studies except there is a 24 h response for significant anti-cancer activity.

Figure 14:
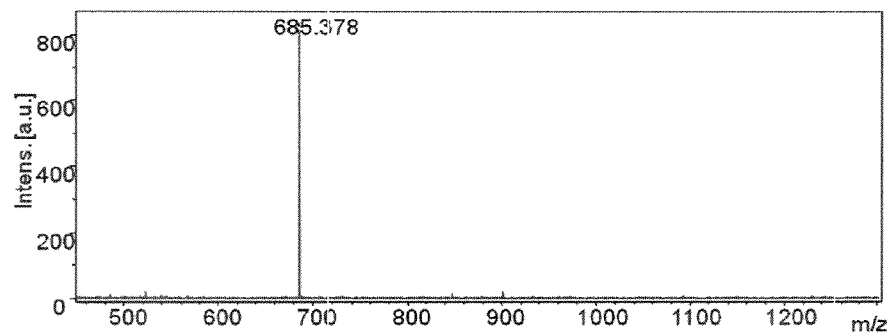
FIG. 14 is a MALDI profile showing molecular weight of the purified bioactive pentapeptide obtained after HPLC purification. x-axis: mass to charge ratio (m/z); and y-axis: intensity. Molecular mass of the peptide identified to be 685.378 daltons. Inset: Purified peak at 62 min elution from HPLC.

MALDI-TOF-MS analysis was performed on the HPLC purified peptide. FIG. 14 shows the MALDI-TOF-MS spectrum of the purified fraction and confirms the purity of the fraction. The accuracy of the mass was confirmed by MALDI-ICR where the mass of the ion was measured to 10 ppm accuracy. By means of MALDI-TOF-MS, single protonated molecular ions (M+H$^+$) of the intact peptide were located at m/z 685.378 for the bioactive pentapeptide.

Figure 15:
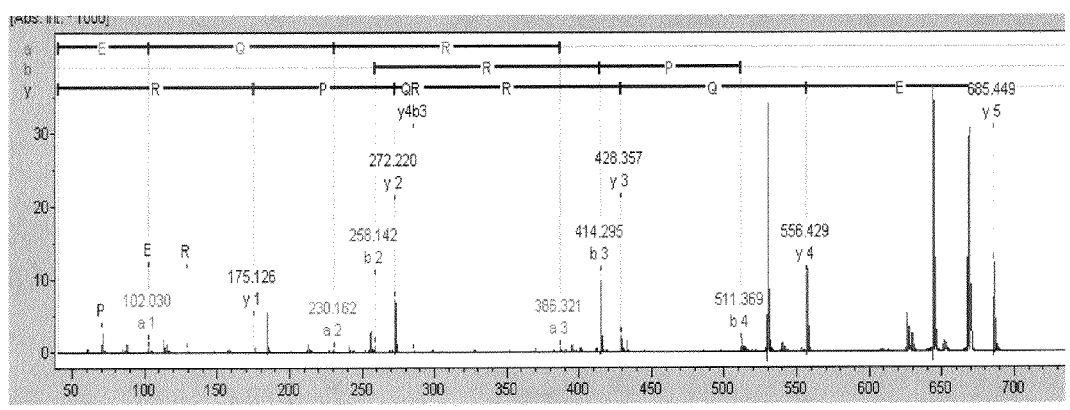
FIG. 15 is a tandem MS-MS PSD fragmentation of the purified bioactive pentapeptide of FIG. 14.

Further tandem MS-MS was performed on the predominant peak by isolating the ion inside the mass spectrometer to enable post source decay fragmentation to obtain amino acid sequence (FIG. 15). Three (3) amino acids were identified from the C-terminus end as Arg-Pro-Arg. The N-terminal amino acids when matched against the database showed a high prediction of Glu-Gln amino acids in the N-terminus end. Table 2 below illustrates de novo sequencing of peptide matched for sequence based on exact mass of 685.378 Da.

TABLE 2

|   | E | Q | R | P | R | Glu | Gln | Arg | Pro | Arg |
|---|---|---|---|---|---|---|---|---|---|---|
| Ion | 1 | 2 | 3 | 4 | 5 | 1 | 2 | 3 | 4 | 5 |
| a | E | Q | R | P | R | 102.055 | 230.114 | 386.215 | 483.267 | 639.369 |
| b | E | Q | R | P | R | 130.050 | 258.108 | 414.210 | 511.262 | 667.363 |
| y | E | Q | R | P | R | 175.119 | 272.172 | 428.273 | 556.331 | 685.374 |
| i | E | Q | R | P | R | 102.055 | 101.070 | 129.113 | 70.065 | 129.113 |
|   |   | 5 | 4 | 3 | 2 | 1 | Arg | Pro | Arg | Gln | Glu |

The de novo sequencing thus revealed the peptide to have the amino acid sequence as Glu-Gln-Arg-Pro-Arg (EQRPR) (SEQ ID NO: 1). The presence of charged (glutamic acid) and heterocyclic amino acid (proline) in the sequence could have attributed anti-cancer properties to the peptide.

Anti-Obesity and Anti-Alzheimer's Properties of Bioactive Pentapeptide Isolated from Heat Stabilized Defatted Rice Bran The bioactive pentapeptide also possesses the ability to promote wellness through health benefits by reducing the risk of chronic complications including obesity- or age-related diseases, such as Alzheimer's disease. After confirming the anti-cancer properties, the bioactive pentapeptide was again isolated and characterized by fractions of peptides from rice bran for possible inhibitory effects against Alzheimer's and obesity. The bioactive pentapeptides were prepared of protein/peptide hydrolysates from rice bran by treating the hydrolysates with simulated GI environments to obtain GI resistant peptides fractionate the resistant peptides to ultrafiltration to generate peptide fractions based on molecular size, evaluate the roles of resistant peptide fractions for bioactivities against obesity and Alzheimer's disease using cell culture models, and finally characterize peptide(s) using chromatography and mass spectrometry.

Minimal hydrolysis and GI juices treatment followed by fractionation resulted in <5 and 5-10 kDa fractions. With <5 and 5-10 kDa fractions the preadipocytes showed differentiation and proliferation (60%) significantly more compared to undifferentiated cells (controls) (25%). Approximately 35% reduction in cytotoxicity of amyloid-induced neuroblastoma cells that were treated with peptide fractions <5 and 5-10 kDa compared to the cytotoxicity was observed with amyloid-induced cells (control) that were not treated with peptides. The bioactive pentapeptide, Glu-Gln-Arg-Pro-Arg (EQRPR) (SEQ ID NO: 1), was characterized from the <5 kDa fraction showing bioactive effects. It showed nearly 70% adipocyte viability more than control possibly signifying insulin-like differentiation to confer protective role against obesity. In addition, the bioactive pentapeptide showed nearly a 45% reduction in cell cytotoxicity on amyloid-induced neuronal cells. The bioactive pentapeptide provides an efficient and reproducible biocatalytic technology that utilizes an underutilized co-product, rice bran, to produce anti-Alzheimer's and anti-obese value-added bioactive peptide, which can be incorporated into pharmaceutical, nutraceutical and food compositions having at least the bioactive pentapeptide as an active ingredient.

Materials: Unless otherwise noted, the materials utilized where the same as enumerated in the forgoing examples of the bioactive pentapeptide and use thereof. Human pre-adipocytes and adipocyte basal growth medium and differentiation medium (Lonza, USA), Neuroblastoma cell line (IMR-32) and growth medium (ATCC, Manassas, USA), and media supplements including fetal bovine serum, gentamycin, were purchased from Hyclone (Logan, Utah). Preparative liquid chromatography system LC-8A was purchased from Shimadzu, USA.

Preparation of Rice Bran Peptide Fractions: HDRB was enzymatically hydrolyzed with food grade Alcalase under optimum degree of hydrolysis following a response surface design to obtain protein hydrolysates. The hydrolysates were treated with simulated GI resistant solutions to generate GI resistant peptides, which were then fractionated into <5, 5-10, 10-50, and >50 kDa fractions as fully discussed above.

Evaluation of Degree of Differentiation of Adipocytes for Accumulation of Lipids: Undifferentiated human preadipocytes were allowed to differentiate upon treatment with a known differentiating agent [0.25 μmol/L DEX (IS-IBMX-DEX) mixture]. To determine the role of peptide fractions on adipocyte differentiation, peptide fractions were added to substitute for insulin or supplemented to DEX mixture. Microscopic observation of accumulation of lipids using a phase contrast microscope (Tissue culture facility, University of Arkansas) as well as glucose uptake if any, were determined to record the degree of differentiation and hence, anti-obese property, if any on the peptide fractions. A trypan blue dye exclusion assay was conducted to determine the adipocyte cell viabilities before and after differentiation upon treatments with the peptides.

Evaluation of Anti-Alzheimer's Disease Activity: Human neuroblastoma cells (IMR-32-ATCC Number CCL-127) was used as model system to evaluate the protective role of rice bran peptide fractions against amyloid beta (1-42) (Cat. No. PP69, EMD Chemicals, Inc., San Diego, Calif.) dependent toxicity. Human neuroblastoma cells were grown in the presence of beta amyloid peptide with and without bran peptide fractions at different levels. Cell survival to the amyloid-induced neuroblastoma cells upon bran peptide treatments was examined by the MTS [(3-(4,5-dimethylthiazole-2-yl)-5-(3-carboxymethoxyphenyl)-2-(4-sulfophenyl)-2H-tetrazolium, inner salt] assay, and compared to the cytotoxicity observed with amyloid-induced neuroblastoma cells.

Purification and Characterization of the Bioactive Pentapeptide Isolated from the <5 kDa Fraction: As fully discussed above, ion exchange chromatography and reverse-phase HPLC were employed to purify the bioactive pentapeptide fully characterized using mass spectrometry and amino acid sequencing.

EXAMPLE 7

Anti-Obesity Effect

Figure 16:
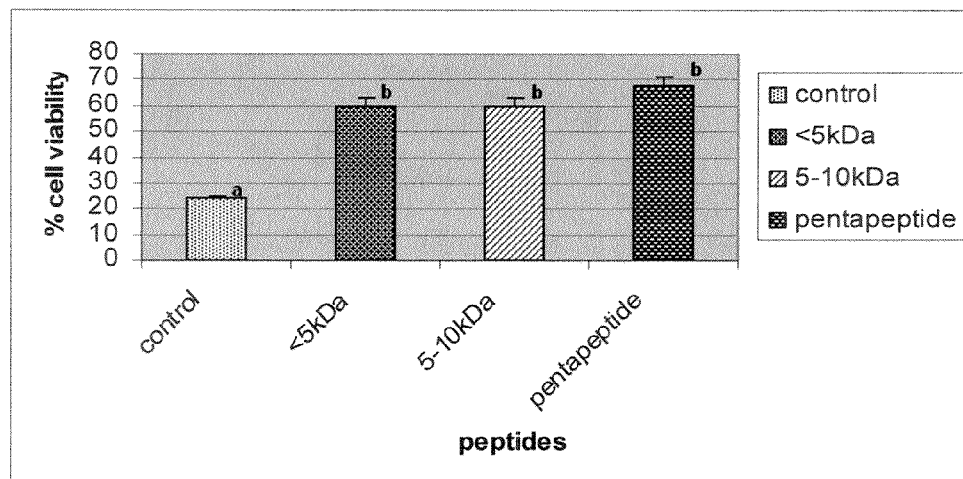
FIG. 16 is a graphical representation of cell viability of adipocytes upon treatment with the purified bioactive pentapeptide from rice bran peptide <5 kDa fractions. The values are means of three (3) replications with standard deviations, and the cell viability was measured using the trypan blue dye exclusion assay.

Obesity results in lipid accumulation and differentiation in adipocytes. Observation of lipid accumulation and rate of differentiation of adipocytes upon treatment with peptide fractions can determine anti-obese property (non or reduced differentiation of adipocytes) of peptide fractions, if any. Visceral preadipocytes were allowed to grow in the presence of peptide fractions without the differentiating factor. The degree of differentiation into adipocytes was observed visually, and cell counts were taken by trypan blue dye exclusion assay. With <5 and 5-10 kDa fractions, the preadipocytes showed differentiation and proliferation significantly more compared to undifferentiated cells (controls). FIG. 16 shows that nearly 60% cells proliferated better than control (undifferentiated cells (~25% proliferation)), possibly signifying differentiation-inducing characteristics of the HDRB peptide fractions Moreover, the bioactive pentapeptide isolated from the <5 kDa fraction showed nearly 70% adipocyte viability more than control possibly signifying insulin-like differentiation to confer obesity protective role. Most of the obesity regulating peptides (YY) are GI based, where they act like gut hormones (leptin) in conferring protective roles mainly by improving digestion and nutrient absorption. The significance of testing peptide fractions through simulated GI tract adds importance by enabling the peptides to resist GI degradation, an important aspect of all gut-regulating peptides.

EXAMPLE 8

Anti-Alzheimer's Effect

Figure 17:
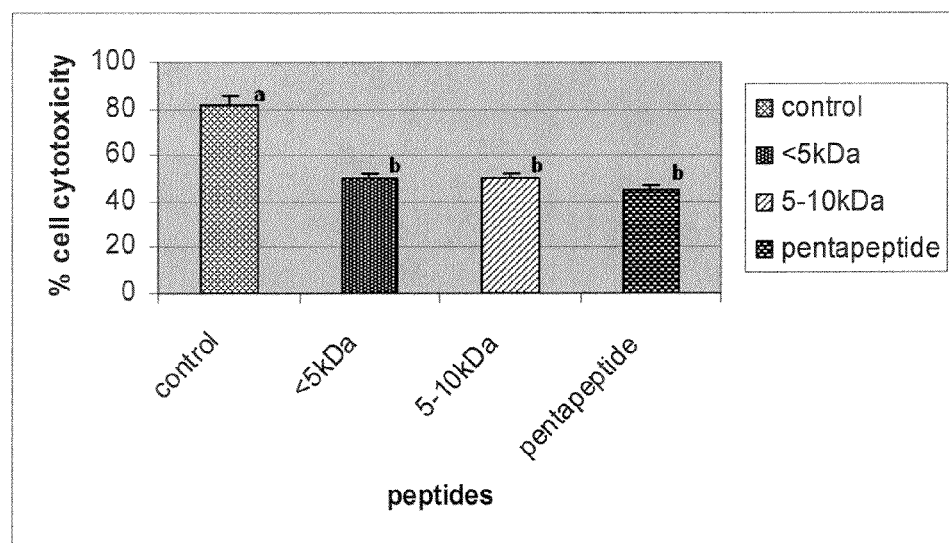
FIG. 17 is a graphical representation of cell viability of amyloid peptide-induced neuronal cells upon treatment with the purified bioactive pentapeptide. The values are means of three (3) replications with standard deviations, and the cell viability was measured using the MTS assay. The control represents amyloid-induced neuronal cells without peptide treatment.

Neuroblastoma cells were treated with amyloid peptide followed by treatment with rice bran peptide fractions. Cytotoxicity to the amyloid-induced neuroblastoma cells was examined by the MTS assay. FIG. 17 shows the extent of cytotoxicity observed with amyloid-induced cells with and without peptide treatments.

A nearly 35% reduction was observed in cytotoxicity of amyloid-induced neuroblastoma cells that were treated with peptide fractions <5 and 5-10 kDa compared to the cytotoxicity observed with amyloid-induced cells (control) that were not treated with peptides. The bioactive pentapeptide is able to confer protective role against Alzheimer's pathology, and further the bioactive pentapeptide isolated from rice bran showed nearly 45% reduction in cell cytotoxicity on amyloid-induced neuronal cells better than the control and the <5 kDa fraction.

Modified Bioactive Pentapeptide from Heat Stabilized Defatted Rice Bran

An RSM design with a 3-factorial model was designed to use combinations of pH, RH (relative humidity), temperature and degree of glycosylation to evaluate enhanced anti-cancer activity of a modified (glycosylated) peptide. Peptide-glucose mixture samples were prepared at the following conditions/combinations: RH 55, 65, & 75 at pHs 6, 7 and 8 maintained at 40, 50 and 60° C. temperatures and tested for growth inhibition activity on colon cancer cells. The degree of glycosylation increased with increasing time at varying RH, and achieved a maximum of ~20% degree of glycosylation. As fully discussed below, glycosylated-peptide prepared at RH 55 at pH 7 or 8 showed slightly better cancer cell activity inhibition (~85%) compared to the unmodified bioactive pentapeptide (~80%). The preparation was achieved at 60° C. The bioactive pentapeptide has one glutamine, and hence, only one (1) site for glycosylation, although only ~20% of the bioactive pentapeptide was glycosylated with D-glucose. Other glycosylating agents, such as dextrin, may be utilized to promote increased glycosylation of the bioactive pentapeptide, and hence possibly an enhanced cancer cell growth inhibition.

Optimization for Degree of Glycosylation: The bioactive pentapeptide (0.02 g) (SEQ ID NO: 1) and D-glucose (0.002 g) were dissolved in water to give a 10% (w/v) protein solution. The solution pH was adjusted to varying pHs based on RSM design (6, 7, 8) and stirred for 10 min, and freeze-dried. The freeze-dried mixture was placed on an aluminum plate, and incubated at 50° C. at varying relative humidity (45%, 65%, 75%) based on the RSM design illustrated below in Table 3.

TABLE 3

| Pattern | pH | RH | Temp | Glycos |
|---|---|---|---|---|
| 0--0 | 7 | 45 | 40 | 30 |
| +00- | 8 | 60 | 50 | 10 |
| -0-0 | 6 | 60 | 40 | 30 |
| 0-0+ | 7 | 45 | 50 | 50 |
| 0000 | 7 | 60 | 50 | 30 |
| 0+0- | 7 | 75 | 50 | 10 |
| 0-0- | 7 | 45 | 50 | 10 |
| 00+- | 7 | 60 | 60 | 10 |
| 0000 | 7 | 60 | 50 | 30 |
| +0+0 | 8 | 60 | 60 | 30 |
| +0-0 | 8 | 60 | 40 | 30 |
| 00++ | 7 | 60 | 60 | 50 |
| 0++0 | 7 | 75 | 60 | 30 |
| -00+ | 6 | 60 | 50 | 50 |
| +-00 | 8 | 45 | 50 | 30 |
| -0+0 | 6 | 60 | 60 | 30 |
| -00- | 6 | 60 | 50 | 10 |
| -+00 | 6 | 75 | 50 | 30 |
| 0+-0 | 7 | 75 | 40 | 30 |
| +00+ | 8 | 60 | 50 | 50 |
| 0+0+ | 7 | 75 | 50 | 50 |
| 00-- | 7 | 60 | 40 | 10 |
| 0-+0 | 7 | 45 | 60 | 30 |
| ++00 | 8 | 75 | 50 | 30 |
| 00-+ | 7 | 60 | 40 | 50 |
| 0000 | 7 | 60 | 50 | 30 |
| --00 | 6 | 45 | 50 | 30 |
| +0+0 | 8 | 60 | 60 | 80 |
| --00 | 6 | 45 | 50 | 80 |
| 0--0 | 7 | 45 | 40 | 80 |
| 0-0+ | 7 | 45 | 50 | 100 |
| 0+-0 | 7 | 75 | 40 | 80 |
| +-00 | 8 | 45 | 50 | 80 |
| +00- | 8 | 60 | 50 | 60 |
| 00+- | 7 | 60 | 60 | 60 |
| +00+ | 8 | 60 | 50 | 100 |
| 0000 | 7 | 60 | 50 | 80 |
| 0+0- | 7 | 75 | 50 | 60 |
| -00- | 6 | 60 | 50 | 60 |
| -+00 | 6 | 75 | 50 | 80 |
| ++00 | 8 | 75 | 50 | 80 |
| 0+0+ | 7 | 75 | 50 | 100 |
| -00+ | 6 | 60 | 50 | 100 |
| 00++ | 7 | 60 | 60 | 100 |
| 0000 | 7 | 60 | 50 | 80 |
| 0-+0 | 7 | 45 | 60 | 80 |
| +0-0 | 8 | 60 | 40 | 80 |
| 0000 | 7 | 60 | 50 | 80 |
| 0++0 | 7 | 75 | 60 | 80 |
| 00-- | 7 | 60 | 40 | 60 |
| 00-+ | 7 | 60 | 40 | 100 |
| -0+0 | 6 | 60 | 60 | 80 |
| 0-0- | 7 | 45 | 50 | 60 |
| -0-0 | 6 | 60 | 40 | 80 |

The RSM design is a 3-factorial model designed to use combinations of pH, RH, temperature and degree of glycosylation and evaluate the best combination that shows enhanced anti-cancer activity as response.

Degree of Glycosylation Determination: Degree of glycosylation of the glycosylated bioactive pentapeptide was determined using a fluorescamine assay. The freeze dried peptide-glucose mixtures were dispersed into 10 mL of deionized water, stirred continuously for 30 min, and filtered through a 0.45 μm syringe filter. The filtrate was diluted 20 times, and 200 μL of the diluted filtrate was added with 4 mL of borate buffer (0.02 M potassium tetraborate, pH 8.5) and 1 mL of fluorescamine reagent (15 mg in 100 mL acetone), and vortexed. Blank solution was prepared using the buffer without the bioactive pentapeptide. Fluorescence intensity was read after 5 min of reaction time using a spectrofluorophotometer (Shimadzu Model RF-1501, Kyoto, Japan) at excitation and emission wavelengths of 390 and 475, respectively.

The degree of glycosylation was calculated as follows:

Degree of glycosylation (%)=$(Ac-Aa)/Ac \times 100$ where Ac was the fluorescence of unmodified protein and Aa was the fluorescence of the glycosylated peptide.

Figure 21:
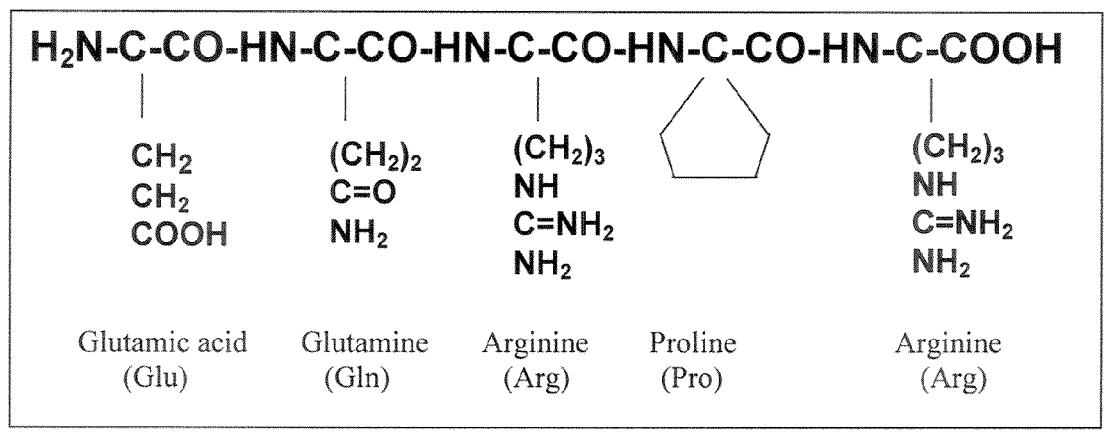
FIG. 21 illustrates an example of the structure of the bioactive pentapeptide isolated and characterized from rice bran having multiple site anti-proliferative activity against cancers, obesity and Alzheimer's disease in accordance with an illustrative embodiment of the bioactive pentapeptides from rice bran and use thereof disclosed herein.

In addition to glycosylation, the bioactive pentapeptide may be subject to other modifications set forth below. Based on the structure of the bioactive pentapeptide having two (2) arginines, a single glutamine and a single glutamic acid, the side chains of the glutamic acid, glutamine, and arginine may be modified (FIG. 21). Because of the lack of lysine amino acid, certain modifications, such as acylation, succinylation and myristolylation, may not be achieved. The following additional modifications can be done for the bioactive pentapeptide.

The side chains of glutamic acid and glutamine can be modified to form pyroglutamate, especially since the bioactive pentapeptides have glutamic acid followed by glutamine in the N-terminal region. Pyroglutamate peptides have been implicated to add functional roles, and have been identified in food protein hydrolysates and are being prepared in industrial scales. Pyroglutamic acid belongs to constituents of generally recognized as safe herbs and plants, and hence can be useful for application in food systems. In order for pyroglutamic acid formation, the bioactive pentapeptide solution is maintained at varying temperatures in a water bath (30-60° C.) for up to 4 h or autoclaved at 121° C. at 15 psi for 30 min. A response surface design would aid in the selection of conditions favorable for pyroglutamate formation.

The side chain of arginine of the bioactive pentapeptide may also be modified. Dicarbonyls used to modify arginines include 2,3-butanedione, p-hydroxyphenylglyoxal and 1,2-cyclohexanedione. Of these, butanedione and cyclohexanedione are approved as food grade chemicals. Hence, to modify the arginine group present in the peptide, butanedione and cyclohexanedione can be used, such as by preparing 10 mM solution of 2,3-butanedione/1,2-cyclohexanedione in water and adjust pH to approximately 9.0. Ten microliters (10 µl) aliquot of the solution is added to 50 µl aliquots of peptide solution (10 mM), which is then incubatated for 60-180 min. The modified sample is passed through a sepandex-iec column and elute with deionized water. The number of modified arginines can be determined by measuring the absorbance of the purified modified peptide at 340 nm.

In addition, the bioactive pentapeptide may be modified by deamidation of glutamine. Deamidation may be achieved at neutral pH when the peptide solution (10 mM) is left at 37° C., in 0.15 M Tris HCl for 24-72 h. The modified bioactive pentapeptide can be examined with time after eluting from a sephadex IEC column, and change in mass identified by mass spectroscopy. The bioactive pentapeptide could also be modified by methylation of glutamine. The methylated bioactive pentapeptide could be formed by preparing 1 M iodoacetamide (IAM) or S-adenosyl methionine (SAM) stock solution in deionized water. Then, a 1 M Formaldehyde stock solution in deionized water is prepared, and 20 µl of 1M IAM or SAM solution is added followed by 40 µL of 1 M formaldehyde solution to 10 µl peptide sample (~1 mg/ml). The solution is then incubated at 4° C. in dark on a gel shaker maintained at 100 rpm for 2 h, at which point a size exclusion chromatography can be performed on the methylated-modified bioactive peptide using 20 m M Tris, 150 mM NaCl, pH 8.0 for buffer exchange and elution. The methylated-modified bioactive peptide using SDS PAGE and mass spectroscopy.

EXAMPLE 9

Anti-Cancer Activity of Glycosylated Bioactive Pentapeptide

Figure 18:
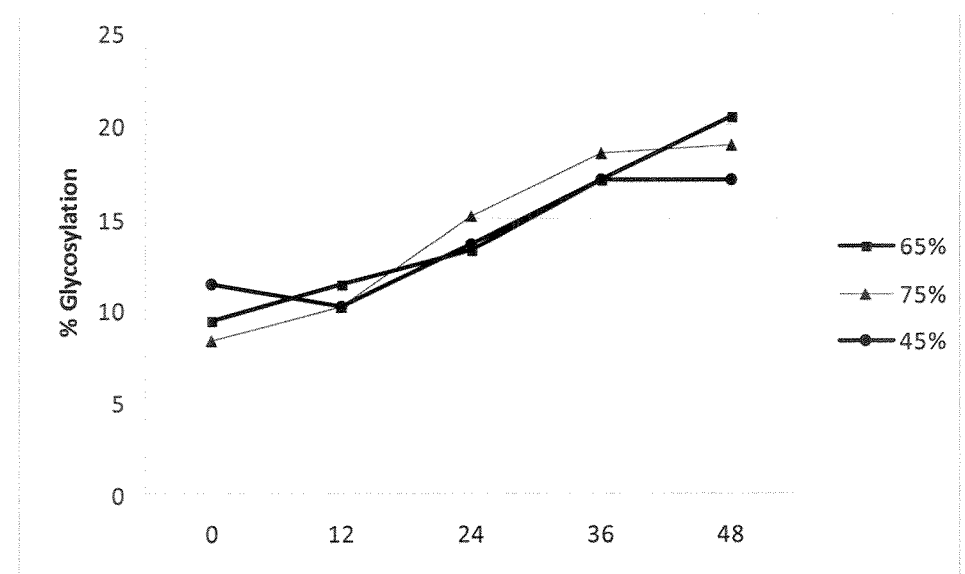
FIG. 18 is a graphical representation of the degree of glycosylation observed with increasing time at varying relative humidity (RH) fractions in accordance with an illustrative embodiment of the bioactive pentapeptides from rice bran and use thereof disclosed herein. Peptide-glucose mixture samples were drawn every 12 h to determine degree of glycosylation at varying RH. Plotted values are mean of triplicate analysis.
Figure 19A:
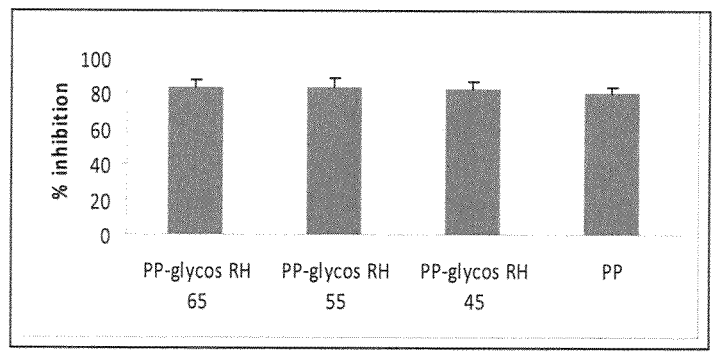
FIGS. 19a, 19b and 19c are graphical representations of the evaluation of enhanced inhibition of glycos-peptides prepared at varying conditions in accordance with an illustrative embodiment of the bioactive pentapeptides from rice bran and use thereof disclosed herein.
Figure 19B:
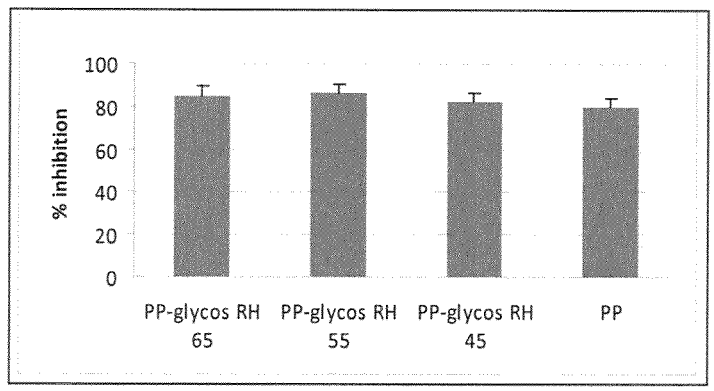
Figure 19C:
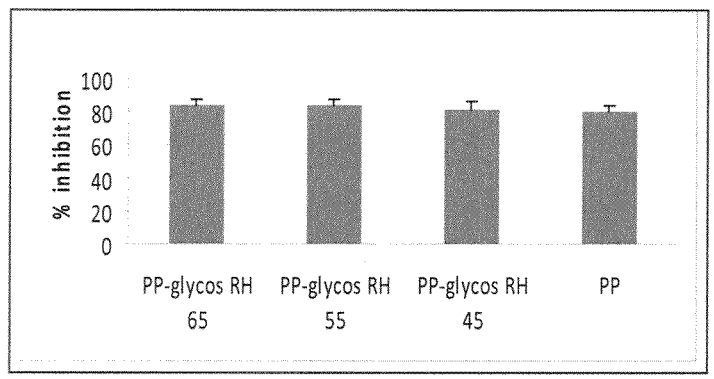
Figure 20:
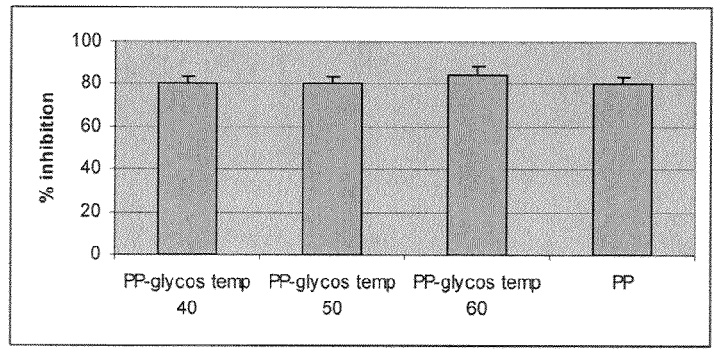
FIG. 20 is a graphical representation of evaluation of enhanced inhibition of glycos-peptide prepared at varying temperatures at pH 7, RH 55. Peptide-glucose mixture samples were prepared at RH 55, pH 7 at 40, 50 and 60° C. temperatures and tested for growth inhibition activity on colon cancer cells. Plotted values are means with standard deviations.

Based on the results illustrated in FIGS. 18 through 20, the modified (glycosylated) bioactive pentapeptide prepared at RH 55 at pH 7 or 8 showed slightly better cancer cell activity inhibition (~85%) compared to the unmodified bioactive pentapeptide (~80%). The preparation was achieved at 60° C. Other temperatures were also tested based on the RSM design, and the following results pertain to the modified bioactive pentapeptide prepared at different temperatures at one particular RH and pH that showed better anticancer activity.

Glycosylated proteins and peptides have been shown to improve functionality in certain food systems owing to the presence of specific groups in amino acid side chains that are sites for modification. The amino acid side chains play a major role in modification reactions, and have been shown to alter the structural integrity of the protein or peptide, thus influencing functionality. In general, proteins and peptides containing amide-rich arginine and glutamine can be subjected to glycosylation modifications. Again, the glycosylated bioactive pentapeptide has one glutamine and hence was the only site for glycosylation, although only ~20% of the peptide was glycosylated with D-glucose. There was nearly 5% increase in bioactive (anti-cancer) property of modified (glycosylated) bioactive pentapeptide. At a glycosylating degree of 20%, glucose-peptide mixture prepared at pH 7 and 8, maintained at RH 55 and temperature 60° C. showed an increase of cancer inhibiting property by 5% compared to the unmodified bioactive pentapeptide. Other glycosylating agents, such as dextrin, may be utilized to promote increased glycosylation of the peptide, and hence possibly an enhanced cancer cell growth inhibition.

Whereas, the compositions and methods have been described in relation to the drawings and claims, it should be understood that other and further modifications, especially to enhance anti-disease and other health-promoting activities and bioactivities of peptide fractions, pure peptides and modified peptides, apart from those shown or suggested herein, may be made within the spirit and scope of this invention.

What is claimed is:

1. A bioactive pentapeptide comprising the amino acid sequence Glu-Gln-Arg-Pro-Arg (SEQ ID NO: 1).

2. The pentapeptide of claim 1 wherein the bioactive pentapeptide is isolated from heat stabilized defatted rice bran or non-defatted rice bran.

3. The pentapeptide of claim 1 wherein the amino group of the glutamine residue or the amino group of the arginine residue of the bioactive pentapeptide is glycosylated.

4. The pentapeptide of claim 1 wherein the carboxyl group of the glutamic acid residue and the amino group of the glutamine residue of the bioactive pentapeptide are modified to form a pyroglutamate acid-peptide.

5. The pentapeptide of claim 1 wherein the amino group of at least one of the arginine residues of the bioactive pentapeptide is modified with a food grade dicarbonyl substance.

6. The pentapeptide of claim 1 wherein the bioactive pentapeptide is produced by the expression of a recombinant nucleic acid molecule or is chemically synthesized.

7. The pentapeptide of claim 1 wherein the carboxyl group of the glutamic acid residue of the bioactive pentapeptide is methylated.

8. The pentapeptide of claim 1 wherein the amino group of the glutamine residue of the bioactive pentapeptide is modified by deamidation.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial
```

-continued

```
<220> FEATURE:
<223> OTHER INFORMATION: Synthetic peptide

<400> SEQUENCE: 1

Glu Gln Arg Pro Arg
1               5
```